(12) United States Patent
Maltbie et al.

(10) Patent No.: US 9,350,802 B2
(45) Date of Patent: May 24, 2016

(54) SYSTEM AND METHOD FOR SECURE, HIGH-SPEED TRANSFER OF VERY LARGE FILES

(71) Applicants: Dan Maltbie, Sunnyvale, CA (US); Lawrence Ganeshalingam, Los Gatos, CA (US); Patrick Allen, Scotts Valley, CA (US)

(72) Inventors: Dan Maltbie, Sunnyvale, CA (US); Lawrence Ganeshalingam, Los Gatos, CA (US); Patrick Allen, Scotts Valley, CA (US)

(73) Assignee: Annia Systems Inc.

( * ) Notice: Subject to any disclaimer, the term of this patent is extended or adjusted under 35 U.S.C. 154(b) by 87 days.

(21) Appl. No.: 13/925,747

(22) Filed: Jun. 24, 2013

(65) Prior Publication Data

US 2014/0164515 A1    Jun. 12, 2014

Related U.S. Application Data

(60) Provisional application No. 61/662,996, filed on Jun. 22, 2012.

(51) Int. Cl.
*G06F 15/16* (2006.01)
*H04L 29/08* (2006.01)

(52) U.S. Cl.
CPC .............. *H04L 67/104* (2013.01); *H04L 67/06* (2013.01); *H04L 67/108* (2013.01); *H04L 67/1063* (2013.01)

(58) Field of Classification Search
CPC .............................. H04L 67/06; H04L 67/322
USPC .................................................. 709/203, 204
See application file for complete search history.

(56) References Cited

U.S. PATENT DOCUMENTS

| | | |
|---|---|---|
| 5,668,810 A | 9/1997 | Cannella, Jr. |
| 6,119,120 A | 9/2000 | Miller |
| 6,582,932 B1 | 6/2003 | Fukiage et al. |
| 6,920,396 B1 | 7/2005 | Wallace et al. |
| 7,158,892 B2 | 1/2007 | Robson et al. |
| 7,248,582 B2 | 7/2007 | Belgaied et al. |
| 7,292,709 B2 | 11/2007 | Imajo |
| 7,354,720 B2 | 4/2008 | Cuppoletti et al. |
| 7,359,379 B2 | 4/2008 | Jarabek et al. |
| 7,366,352 B2 | 4/2008 | Kravec et al. |
| 7,408,957 B2 | 8/2008 | Calvignac et al. |
| 7,428,554 B1 | 9/2008 | Coberley et al. |

(Continued)

FOREIGN PATENT DOCUMENTS

| | | |
|---|---|---|
| EP | 0429201 | 5/1991 |
| KR | 10-2007-0115964 | 12/2007 |

(Continued)

OTHER PUBLICATIONS

Office Action for U.S. Appl. No. 12/828,234, mailed May 22, 2012.

(Continued)

*Primary Examiner* — Adnan Mirza
(74) *Attorney, Agent, or Firm* — Cooley LLP

(57) ABSTRACT

A method for parallelized transfer of an electronic file over a network. The method includes sending a first portion of the electronic file from a first sending node and receiving, at the first sending node, information relating to a second portion of the electronic file sent by a second sending node. The method further includes sending a third portion of the electronic file from the first sending node, wherein the third portion is different from the second portion.

17 Claims, 16 Drawing Sheets

(56) References Cited

U.S. PATENT DOCUMENTS

| | | | |
|---|---|---|---|
| 7,467,219 B2 | 12/2008 | Hodges et al. | |
| 7,739,390 B2 | 6/2010 | Brahmbhatt et al. | |
| 7,820,378 B2 | 10/2010 | van den Boom et al. | |
| 7,856,317 B2 | 12/2010 | Schilling | |
| 7,885,969 B2 | 2/2011 | Natarajan et al. | |
| 7,996,876 B1 | 8/2011 | Everson et al. | |
| 8,412,462 B1 | 4/2013 | Ganeshalingam et al. | |
| 8,606,846 B2 * | 12/2013 | Czechowski et al. | 709/203 |
| 8,982,879 B2 | 3/2015 | Ganeshalingam et al. | |
| 2002/0029113 A1 | 3/2002 | Wang et al. | |
| 2002/0103937 A1 | 8/2002 | Tillmann et al. | |
| 2002/0111742 A1 | 8/2002 | Rocke et al. | |
| 2003/0039362 A1 | 2/2003 | Califano et al. | |
| 2003/0055824 A1 | 3/2003 | Califano et al. | |
| 2003/0082544 A1 | 5/2003 | Fors et al. | |
| 2003/0097227 A1 | 5/2003 | Bloch et al. | |
| 2003/0113756 A1 | 6/2003 | Mertz | |
| 2003/0224419 A1 | 12/2003 | Corcoran et al. | |
| 2003/0236393 A1 | 12/2003 | Trucksis | |
| 2004/0003132 A1 | 1/2004 | Stanley et al. | |
| 2004/0005558 A1 | 1/2004 | Anderson et al. | |
| 2004/0006433 A1 | 1/2004 | Robson et al. | |
| 2005/0049795 A1 | 3/2005 | Fikuda et al. | |
| 2005/0053968 A1 | 3/2005 | Bharadwaj et al. | |
| 2005/0060599 A1 | 3/2005 | Inami et al. | |
| 2005/0075794 A1 | 4/2005 | Hoffmann et al. | |
| 2005/0119535 A1 | 6/2005 | Yanagihara et al. | |
| 2005/0131649 A1 | 6/2005 | Larsen et al. | |
| 2005/0164247 A1 | 7/2005 | Brunkow et al. | |
| 2005/0181362 A1 | 8/2005 | Apolito et al. | |
| 2005/0267693 A1 | 12/2005 | Allard et al. | |
| 2005/0267971 A1 | 12/2005 | Fritz | |
| 2006/0224687 A1 * | 10/2006 | Popkin et al. | 709/217 |
| 2006/0285685 A1 | 12/2006 | Msezane | |
| 2007/0026406 A1 | 2/2007 | El Ghaoui et al. | |
| 2007/0042372 A1 | 2/2007 | Arita | |
| 2007/0101154 A1 | 5/2007 | Bardsley et al. | |
| 2007/0148658 A1 | 6/2007 | Nelson et al. | |
| 2007/0168135 A1 | 7/2007 | Agarwal et al. | |
| 2007/0190534 A1 | 8/2007 | Birch-Machin et al. | |
| 2007/0271604 A1 | 11/2007 | Webster et al. | |
| 2007/0288172 A1 | 12/2007 | Aronow et al. | |
| 2008/0016201 A1 | 1/2008 | Thompson | |
| 2008/0077607 A1 | 3/2008 | Gatawood et al. | |
| 2008/0255877 A1 | 10/2008 | Fernandez | |
| 2008/0271053 A1 | 10/2008 | Kramer et al. | |
| 2008/0281818 A1 | 11/2008 | Tenenbaum et al. | |
| 2009/0203986 A1 | 8/2009 | Winnick | |
| 2010/0014496 A1 | 1/2010 | Kalika et al. | |
| 2010/0050253 A1 | 2/2010 | Baughman et al. | |
| 2010/0135488 A1 | 6/2010 | Lee et al. | |
| 2010/0161607 A1 | 6/2010 | Singh et al. | |
| 2010/0169107 A1 | 7/2010 | Ahn et al. | |
| 2010/0169313 A1 | 7/2010 | Kenedy et al. | |
| 2010/0169338 A1 | 7/2010 | Kenedy et al. | |
| 2010/0169340 A1 | 7/2010 | Kenedy et al. | |
| 2010/0262718 A1 | 10/2010 | Ikeno et al. | |
| 2012/0047202 A1 | 2/2012 | Van Ackere et al. | |
| 2012/0089339 A1 | 4/2012 | Ganeshalingam et al. | |
| 2012/0089603 A1 | 4/2012 | Ganeshalingam et al. | |
| 2012/0089607 A1 | 4/2012 | Ganeshalingam et al. | |
| 2012/0089608 A1 | 4/2012 | Ganeshalingam et al. | |
| 2012/0089652 A1 | 4/2012 | Ganeshalingam et al. | |
| 2012/0095693 A1 | 4/2012 | Ganeshalingam et al. | |
| 2012/0230326 A1 | 9/2012 | Ganeshalingam et al. | |
| 2012/0230338 A1 | 9/2012 | Ganeshalingam et al. | |
| 2012/0230339 A1 | 9/2012 | Ganeshalingam et al. | |
| 2012/0232874 A1 | 9/2012 | Ganeshalingam et al. | |
| 2012/0233201 A1 | 9/2012 | Ganeshalingam et al. | |
| 2012/0233202 A1 | 9/2012 | Ganeshalingam et al. | |
| 2012/0236861 A1 | 9/2012 | Ganeshalingam et al. | |
| 2013/0246460 A1 | 9/2013 | Maltbie et al. | |
| 2014/0164516 A1 | 6/2014 | Maltbie et al. | |

FOREIGN PATENT DOCUMENTS

| | | |
|---|---|---|
| WO | WO 97/22076 | 6/1997 |
| WO | WO 2004/015579 | 2/2004 |
| WO | WO 2006/084391 | 8/2006 |
| WO | WO 2006/102128 | 9/2006 |

OTHER PUBLICATIONS

Office Action for U.S. Appl. No. 12/828,234, mailed Mar. 13, 2013.
Office Action for U.S. Appl. No. 12/837,452, mailed Apr. 5, 2012.
Office Action for U.S. Appl. No. 13/223,071, mailed Nov. 13, 2013.
International Search Report and Written Opinion for International Application No. PCT/US2011/050073, mailed Apr. 25, 2012.
Office Action for U.S. Appl. No. 13/223,077, mailed Nov. 20, 2012.
International Search Report and Written Opinion for International Application No. PCT/US2011/050075, mailed Apr. 25, 2012.
Office Action for U.S. Appl. No. 13/223,084, mailed May 12, 2014.
Office Action for U.S. Appl. No. 13/223,084, mailed Sep. 27, 2013.
Office Action for U.S. Appl. No. 13/223,084, mailed Feb. 7, 2013.
International Search Report and Written Opinion for International Application No. PCT/US2011/050077, mailed Apr. 27, 2012.
Office Action for U.S. Appl. No. 13/223,088, mailed Jan. 2, 2013.
International Search Report and Written Opinion for International Application No. PCT/US2011/050078, mailed Mar. 21, 2012.
Office Action for U.S. Appl. No. 13/223,092, mailed May 12, 2014.
Office Action for U.S. Appl. No. 13/223,092, mailed Sep. 6, 2013.
Office Action for U.S. Appl. No. 13/223,092, mailed Feb. 7, 2013.
International Search Report and Written Opinion for International Application No. PCT/US2011/050079, mailed Apr. 9, 2012.
Office Action for U.S. Appl. No. 13/223,097, mailed Sep. 18, 2013.
Office Action for U.S. Appl. No. 13/223,097, mailed Nov. 16, 2012.
International Search Report and Written Opinion for International Application No. PCT/US2011/050080, mailed May 1, 2012.
Office Action for U.S. Appl. No. 13/290,992, mailed Sep. 13, 2013.
Office Action for U.S. Appl. No. 13/417,184, mailed Nov. 26, 2013.
International Search Report and Written Opinion for International Application No. PCT/US2012/028642, mailed Oct. 23, 2012.
International Search Report and Written Opinion for International Application No. PCT/US2012/028643, mailed Sep. 3, 2012.
Office Action for U.S. Appl. No. 13/417,188, mailed Nov. 4, 2013.
International Search Report and Written Opinion for International Application No. PCT/US2012/028644, mailed Sep. 3, 2012.
Office Action for U.S. Appl. No. 13/417,189, mailed Nov. 4, 2013.
International Search Report and Written Opinion for International Application No. PCT/US2012/028645, mailed Sep. 3, 2012.
Office Action for U.S. Appl. No. 13/417,190, mailed Nov. 29, 2013.
International Search Report and Written Opinion for International Application No. PCT/US2012/028647, mailed Sep. 26, 2012.
Office Action for U.S. Appl. No. 13/417,192, mailed Mar. 26, 2014.
Office Action for U.S. Appl. No. 13/417,192, mailed Aug. 30, 3013.
International Search Report and Written Opinion for International Application No. PCT/US2012/028650, mailed Sep. 27, 2012.
Office Action for U.S. Appl. No. 13/417,193, mailed Feb. 13, 2014.
Office Action for U.S. Appl. No. 13/417,193, mailed May 23, 2013.
International Search Report and Written Opinion for International Application No. PCT/US2012/028652, mailed Oct. 23, 2012.
International Search Report and Written Opinion for International Application No. PCT/US2012/057668, mailed Jan. 17, 2013.
International Search Report and Written Opinion for International Application No. PCT/US2013/047438, mailed Nov. 1, 2013.
Calabretta, N. et al., "Optical Signal Processing Based on Self-Induced Polarization Rotation in a Semiconductor Optical Amplifier," Journal of Lightwave Technology, 22(2):372-381 (Feb. 2004).
UHN Human CpG Island Microarray Database Searches [online], Retrieved from the Internet on Sep. 28, 2011 and Oct. 3, 2011, <URL: http://data.microarrays.ca/cpg/index.htm>, 16 pages.
Tanenbaum, D. M. et al., "The JCVI Standard Operating Procedure for Annotating Prokaryotic Metagenmic Shotgun Sequencing Data," Standards in Genomic Sciences, 2(2):229-237 (Apr. 2010).
Office Action for U.S. Appl. No. 12/828,234, mailed Sep. 8, 2014, 32 pages.

(56) References Cited

OTHER PUBLICATIONS

Office Action for U.S. Appl. No. 13/223,071, mailed Jun. 5, 2014, 15 pages.
Office Action for U.S. Appl. No. 13/223,071, mailed Dec. 26, 2014, 14 pages.
Office Action for U.S. Appl. No. 13/223,084, mailed Aug. 6, 2014, 10 pages.
Office Action for U.S. Appl. No. 13/223,092, mailed Jun. 25, 2014, 9 pages.
Office Action for U.S. Appl. No. 13/223,092, mailed Jan. 16, 2015, 14 pages.
Office Action for U.S. Appl. No. 13/223,097, mailed Jun. 5, 2014, 8 pages.
Office Action for U.S. Appl. No. 13/223,097, mailed Jan. 7, 2015, 14 pages.
Office Action for U.S. Appl. No. 13/290,992, mailed Aug. 29, 2014, 15 pages.
Office Action for U.S. Appl. No. 13/290,992, mailed Jan. 7, 2015, 11 pages.
Office Action for U.S. Appl. No. 13/417,184, mailed Jun. 16, 2014, 11 pages.
Office Action for U.S. Appl. No. 13/417,187, mailed May 21, 2014, 12 pages.
Office Action for U.S. Appl. No. 13/417,187, mailed Dec. 23, 2014, 13 pages.
Office Action for U.S. Appl. No. 13/417,188, mailed May 29, 2014, 9 pages.
Office Action for U.S. Appl. No. 13/417,189, mailed May 27, 2014, 9 pages.
Office Action for U.S. Appl. No. 13/417,190, mailed Aug. 29, 2014, 10 pages.
Office Action for U.S. Appl. No. 13/417,192, mailed Nov. 19, 2014, 11 pages.
Office Action for U.S. Appl. No. 13/417,193, mailed Sep. 11, 2014, 43 pages.
Networking Tutorial, The CTDP Networking Guide, Version 0.6.3 (Feb. 3, 2001), pp. 1-149.
International Preliminary Report on Patentability for International Application No. PCT/US2011/050073, mailed Mar. 5, 2013.
International Preliminary Report on Patentability for International Application No. PCT/US2011/050075, mailed Mar. 5, 2013.
International Preliminary Report on Patentability for International Application No. PCT/US2011/050077, mailed Mar. 5, 2013.
International Preliminary Report on Patentability for International Application No. PCT/US2011/050078, mailed Mar. 5, 2013.
International Preliminary Report on Patentability for International Application No. PCT/US2011/050079, mailed Mar. 5, 2013.
International Preliminary Report on Patentability for International Application No. PCT/US2011/050080, mailed Mar. 5, 2013.
International Preliminary Report on Patentability for International Application No. PCT/US2012/028642, mailed Sep. 10, 2013.
International Preliminary Report on Patentability for International Application No. PCT/US2012/028643, mailed Sep. 10, 2013.
International Preliminary Report on Patentability for International Application No. PCT/US2012/028644, mailed Sep. 10, 2013.
International Preliminary Report on Patentability for International Application No. PCT/US2012/028645, mailed Sep. 10, 2013.
International Preliminary Report on Patentability for International Application No. PCT/US2012/028647, mailed Sep. 10, 2013.
International Preliminary Report on Patentability for International Application No. PCT/US2012/028650, mailed Sep. 10, 2013.
International Preliminary Report on Patentability for International Application No. PCT/US2012/028652, mailed Sep. 10, 2013.
International Preliminary Report on Patentability for International Application No. PCT/US2012/057668, mailed Apr. 1, 2014.
International Preliminary Report on Patentability for International Application No. PCT/US2013/047438, mailed Dec. 23, 2014.
Office Action for U.S. Appl. No. 13/223,084, mailed Mar. 23, 2015, 11 pages.
Office Action for U.S. Appl. No. 13/925,748, mailed Apr. 14, 2015, 7 pages.
Office Action for U.S. Appl. No. 13/417,189, mailed May 14, 2015, 11 pages.
Notice of Allowance for U.S. Appl. No. 13/417,192, mailed Jun. 9, 2015, 7 pages.
Office Action for U.S. Appl. No. 13/417,184, mailed Jun. 24, 2015, 10 pages.

* cited by examiner

SYSTEM AND METHOD FOR SECURE, HIGH-SPEED TRANSFER OF VERY LARGE FILES

CROSS-REFERENCE TO RELATED APPLICATIONS

The present application claims the benefit of priority under 35 U.S.C. §119(e) of U.S. Provisional Application Ser. No. 61/662,996, entitled SYSTEM AND METHOD FOR SECURE, HIGH-SPEED TRANSFER OF VERY LARGE FILES, filed Jun. 22, 2012, the contents of which is hereby incorporated by reference in its entirety for all purposes.

FIELD

This disclosure generally relates to the transfer of files of large size, and more particularly relates to systems and methods for the secure and high-speed transfer of such files.

BACKGROUND

The transmission control protocol ("TCP") is known to use the additive increase/multiplicative decrease algorithm to avoid congestion and control bandwidth usage. Unfortunately, this aspect of TCP can impede the transmission rate of very large sequence data files, even on high-speed networks.

A "peer-to-peer" network of computers harnesses the bandwidth and computational power of the computers participating in the network. This contrasts with conventional "client-server" approaches, in which computing power and bandwidth are concentrated in a relatively small number of servers. Such peer-to-peer networks may facilitate the transfer of files through a set of connections established between participating peers.

BitTorrent is a popular file distribution program currently used in peer-to-peer networks. A peer within a BitTorrent system may be any computer running an instance of a client program implementing the BitTorrent protocol. Each BitTorrent client is capable of preparing, requesting, and transmitting any type of computer file over a network in accordance with the BitTorrent protocol. BitTorrent is designed to enable distribution of large amounts of data without consuming correspondingly large amounts of computational and bandwidth resources.

To share a file or group of files, a BitTorrent peer first creates a small file called a "torrent" (e.g. "Filename.torrent"). The torrent file contains metadata about the files to be shared and also includes information about a component, termed the "tracker", that coordinates the file distribution. Torrent files are generally published on a website or other accessible network location. The tracker maintains lists of the clients currently participating in the torrent. A peer desiring to download a file of interest must first obtain a copy of the corresponding torrent file and connect to the specified tracker. The tracker then informs the peer from which other peers pieces of the file of interest may be downloaded.

The peer distributing a data file generally treats the file as being comprised of a number of identically-sized pieces, usually with byte sizes of a power of 2, and typically between 32 kB and 16 MB each. The peer creates a hash for each piece, using the SHA-1 hash function, and records the hash value in the torrent file. When another peer later receives a particular piece, the hash of the piece is compared to the recorded hash to test that the piece is free of errors. Peers that provide a complete file are called "seeders", and the peer providing the initial copy of the file may be called the "initial seeder".

The exact information contained in the torrent file depends on the version of the BitTorrent protocol being utilized. In general, torrent files include an "announce" section, which specifies the URL of the tracker. Torrent files also include an "info" section, which contains suggested names for the files, their respective lengths, the piece length used, and a SHA-1 hash code for each piece. This information is used by requesting peers to verify the integrity of the data received.

With respect to a given file, the tracker maintains records of which peers are "seeds" (i.e., a peer having the complete file(s) being distributed) and of the other peers in the applicable "swarm" (i.e., the set of seeds and peers involved in the distribution of the file(s)). During the distribution process peers periodically report information to the tracker and request and receive information concerning other peers to which they may connect. Users interested in obtaining a file or files using BitTorrent may, using a web browser installed on a local machine, navigate to a website listing the torrent and download it. Once downloaded, the torrent may be opened in a BitTorrent client stored on the local machine. Once the torrent is opened, the BitTorrent client establishes a connection with the tracker. At this point the tracker provides the BitTorrent client with a list of peers currently downloading the file or files of interest.

If a BitTorrent client happens to be the first such client interested in a file associated with a torrent, for at least some period of time such client may be the only peer within the swarm and thus connects directly to the initial seeder and requests pieces of the file. As other peers join the swarm, the peers exchange pieces with each other in addition to downloading pieces from the initial seeder.

Unfortunately, in the case of very large files it will generally be rather burdensome for the initial seeder to respond to requests for file pieces from multiple requesting peers. Moreover, limitations on the processing and input/output resources of the initial seeder may impede the efficient and rapid distribution of very large files.

SUMMARY

The present disclosure describes a system and method for secure, high-speed file transfer which is capable of overcoming the disadvantages of TCP and existing peer-to-peer protocols with respect to the distribution of files of very large size. Like other peer-to-peer file distribution systems, the disclosed GeneTorrent™ high-speed file transfer system utilizes a tracker to enable a plurality of peers to cooperatively distribute a file of interest. However, in one aspect the GeneTorrent™ system incorporates a Transactor which is integrated within or otherwise operates in conjunction with the tracker. The Transactor is a program which operates to immediately identify and make a record of those clients (i.e., actors) which request a certain file of interest (e.g., "file X"). The Transactor will also generally be configured to determine the authentication and entitlement of each actor based on authorization rules and using a secure key distribution scheme.

In one embodiment the Transactor clusters individual actors which have requested file X into a cast of participating actors comprising an affinity group. The Transactor may determine which actors are assigned to a particular cast based upon, for example, the file requested, the location of the file (i.e., with which actor(s) the file is currently stored), as well as the credentials of the actors requesting access to the file. Once an actor has been directed to a particular cast, the actor exchanges messages with other actors within the cast in order to determine and receive the portions of the file of interest currently possessed by the cast. Stated differently, the Transactor proactively directs a requesting leecher actor to a feeder affinity group such that the leecher receives as much of the requested file as possible without, to the extent possible, incrementing the burden on the seed of file X.

In the case of very large files, such as files containing genomic or other biological sequence information, the GeneTorrent™ approach effectively "parallelizes" the transfer of file information and reduces the burden on the initial seed or seeds of file X. Moreover, the use of parallel streams within the GeneTorrent™ system minimizes the effect of a multiplicative decrease in the speed of any one stream resulting from the characteristics of TCP discussed above. Thus, use of the GeneTorrent™ approach may reduce the likelihood of bottlenecks developing around overburdened seed servers in connection with the transfer of very large data files.

The use of such parallel streams also enables the separate encryption of each individual file segment, thus obviating the need for re-encryption and retransmission of the entire file in the event of corruption of an individual segment. Particularly in the case of very large data files containing sensitive information (e.g., files containing genomic sequence information), this aspect of the GeneTorrent™ approach may offer considerable advantages relative to existing methods of file distribution.

In one aspect, the present disclosure relates to a method for facilitating transfer of an electronic file over a network. The method includes sending a first portion of the electronic file from a first sending node and receiving, at the first sending node, information relating to a second portion of the electronic file sent by a second sending node. The method further includes sending a third portion of the electronic file from the first sending node, wherein the third portion is different from the second portion.

In a related aspect the method may further include reading the first portion of the electronic file and the third portion of the electronic file from a database containing the electronic file. In addition, the method may further include providing, to the second sending node, information relating to the sending of the first portion of the electronic file. Moreover, the method may include receiving information relating to a fourth portion of the electronic file sent by a third sending node wherein the third portion is different from the fourth portion.

The disclosure also pertains to a method for facilitating transfer of an electronic file over a network. The method includes generating first encrypted file information by encrypting a first portion of the electronic file using first encryption information, wherein the first portion is associated with a first layer of a plurality of layers of information within the electronic file. The method further includes generating second encrypted file information by encrypting a second portion of the electronic file using second encryption information different from the first encryption information, wherein the second portion is associated with a second layer of the plurality of layers of information. In addition, the method includes sending the first encrypted file information from a first sending node and sending the second encrypted file information from a second sending node.

In a further aspect, the present disclosure is directed to a method for facilitating transfer of an electronic file over a network. The method includes receiving, from a first receiving node, a first portion of an electronic file sent by a first sending node. The method further includes receiving, from a second receiving node, a second portion of the electronic file sent by a second sending node.

BRIEF DESCRIPTION OF THE DRAWINGS

For a better understanding of the nature and objects of various embodiments of the invention, reference should be made to the following detailed description taken in conjunction with the accompanying drawings, wherein.

DETAILED DESCRIPTION OF EMBODIMENTS

Introduction

Figure 1:
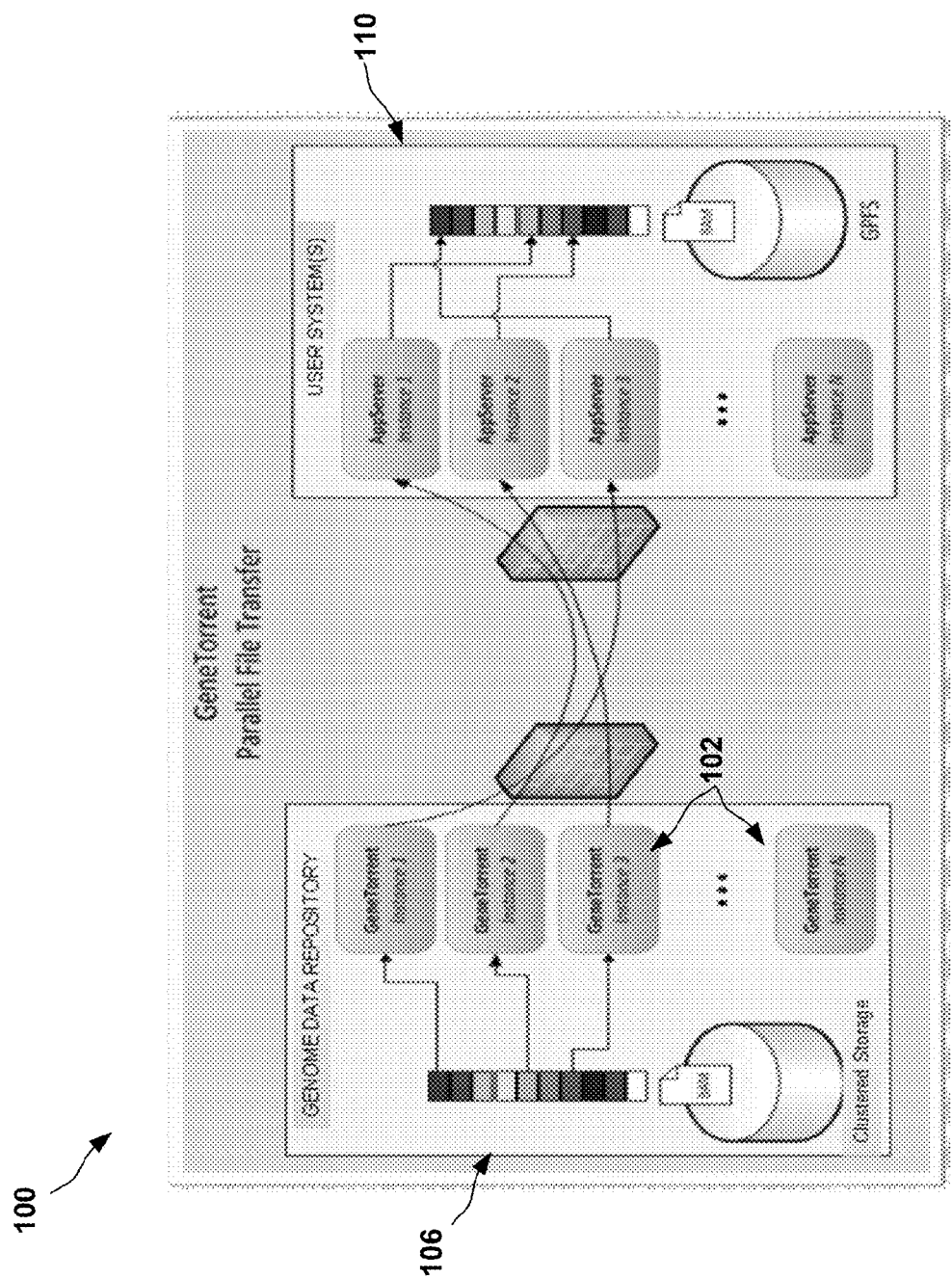
FIG. 1 provides a high-level representation of the architecture of a GeneTorrent™ system configured to form multiple instances of a GeneTorrent™ object file so as to enable a cluster of servers to transfer parallel streams of file information to a user system.

At this early stage in the experimental development of the human genome biology and next generation sequencing (NGS) technology, there is yet still much to be discovered and understood.

For example, one major rate limiting step involves the ineffectiveness on the part of the research community to make decisions as a group to set the highest standards for the genomic data space. For example, it may be particularly important to develop standards around the quality of service that is used to touch genomic, transcriptomic, proteomic and other large volumes of omics data. Moreover, this type of biological data will typically require extreme security considerations. The dataset might contain genotypic and phenotypic information that could have profound effects on an individual if it is breached.

This information also requires special consideration with regards to data integrity and form; that is, the data need high-level validation. It is important that the data is transferred with the highest fidelity. In addition, these are very large datasets where failed transmissions can be costly in time.

Finally, some of this data will need to be conditionally accessible to different sources in various regions for various reasons. For example, if certain regions of the genome are required for breast cancer analysis the regions associated with other phenotypes and or diseases can remain inaccessible.

The approaches disclosed herein use a method to structure GeneTorrent™ Object ("GTO" or ".gto") files so as to allow multiple instances of parallelized streams to be sent and received by two or more actors. Consistent with the GeneTorrent™ protocol disclosed herein, very large biological sequence data files may be transferred at high-speed. In addition, security may be enhanced by applying encryption to parallel streams of N instances of the same GTO file from multiple servers. In one embodiment an entitlement control system may be used in conjunction with the GeneTorrent™ system to regulate authorization of actors and authentication for access to certain .gto files.

GeneTorrent™ Architecture & Characteristics

As is discussed below, in exemplary embodiments GeneTorrent™ system files are fragmented into pieces for parallel independent transfer. The location of multiple sources ("seeders") for a file may be advertised. In addition, actors or other peers may exchange protocol messages containing metadata about files. Exemplary embodiments of the GeneTorrent™ approach contemplate use of a number of unique techniques, including methods for limiting membership in the "swarm" of systems that can be "seeding" a file and requiring each pair of "actors" exchanging data to reciprocally authenticate. These novel techniques further include encrypting data in transit using strong, standard cryptographic technology and constraining peer-to-peer interactions to authenticated users with authorization to perform the requested "seeding" or "leeching" operations on the requested data.

In one embodiment user-level authentication and dataset authorization is performed before peers can initiate a GeneTorrent™ transfer. In this embodiment a GeneTorrent™ peer desiring to initiate a transfer first contacts a control component (hereinafter also termed a "GT Exec") on a GeneTorrent™ repository and passes the user credentials. The GT Exec authenticates that the credentials have not expired and correspond to a known user. The GT Exec may then further verify that the user is authorized to perform the requested action (e.g., upload or download) on the specific data files identified in the request.

GeneTorrent™ Object File Transfer—Multiple Parallel Streams

In one aspect GeneTorrent™ enables multiple sending actors to transfer file pieces to multiple receiving actors over parallel streams. This approach has several advantages. For example, parallel M:N transfers avoid many of the bottlenecks that occur in 1:1 transfers, such as issues with disk I/O, CPU utilization, large bandwidth-delay products in the WAN, and other side-effects of transferring very large data sets. Error detection and error recovery are built in, automatic and very robust. The protocol is content-agnostic, allowing data file formats to evolve without impacting the underlying transfer mechanisms The protocol scales asymmetrically—M:N transfers for high volume producers and 1:N downloaders for the periodic user are supported by the same application. The protocol is capable of saturating the available network bandwidth and reacts well to dynamic changes in the congestion levels in the transport network The GeneTorrent™ protocol is capable of rapidly and efficiently transmitting large biological sequence data files. As a result, in one embodiment a dynamic encryption key distribution system is integrated into the file transfer system to facilitate secure transfers. This allows for encryption of data in multiple layers that can be controlled using a hierarchical entitlement scheme. For example, one GTO file can be encrypted in a format that allows for multiple downloaders to access different layers of data from the files.

Attention is now directed to FIG. 1, which provides a high-level representation of the architecture of a GeneTorrent™ system 100 configured to form multiple instances of a GTO file so as to enable a cluster of servers 102 within or associated with a genome data respository (GDR) 106 to transfer parallel streams of file information to a user system 110. Although not shown in FIG. 1, integrated within or layered "on top of" the architecture is a highly secure encryption system.

Gene Torrent Object Files

In one embodiment an actor first locates a Torrent file describing the target data as an initial step in participating in a GeneTorrent™ parallel file transfer. Such a Torrent file may comprise a static "bencoded" dictionary including the Announce URL, an info dictionary, and other optional fields. In one embodiment GeneTorrent™ uses dynamic one-time Gene Torrent Object files to bootstrap a secure and encrypted file transfer based on bi-directionally authenticated SSL sessions.

In a GeneTorrent™ system, the Torrent file will generally be structured in order to accommodate the efficient transfer of very large files. For example, the task of generating the SHA™ hashes for all the "pieces" of a very large file would be computationally expensive and impose an unnecessary I/O burden on the local storage system. Accordingly, rather than regenerating new SHA™ hashes for every file piece each time a user downloads the file, in one embodiment one or more seeders cache the torrent data for reuse. Each large data file will have an associated static Torrent file which will be stored in the same directory. This torrent file may comprise a "normal" Torrent, i.e., it may lack SSL certificate information. Such certificate information and any other additional data fields may instead be dynamically inserted into the Gene Torrent Object file at the time of a download request, thus creating a one-time-use Torrent with authentication keys.

Transactor

As discussed above, the Transactor at least partially enables a GeneTorrent™ system to transmit a file of interest in multiple parallel streams to a requesting entity. As discussed above, in one embodiment the Transactor clusters individual actors which have requested file X into a cast of participating actors comprising an affinity group. The Transactor may determine which actors are assigned to a particular cast based upon, for example, the file requested, the location of the file (i.e., with which actor(s) the file is currently stored), as well as the credentials of the actors requesting access to the file. Once an actor has been directed to a particular cast, the actor exchanges messages with other actors within the cast in order to determine and receive the portions of the file of interest currently possessed by the cast. That is, a requesting leecher actor is proactively directed to a feeder affinity group such that the leecher receives as much of the requested file as possible without, to the extent possible, incrementing the burden on the seed of file X.

Figure 2:
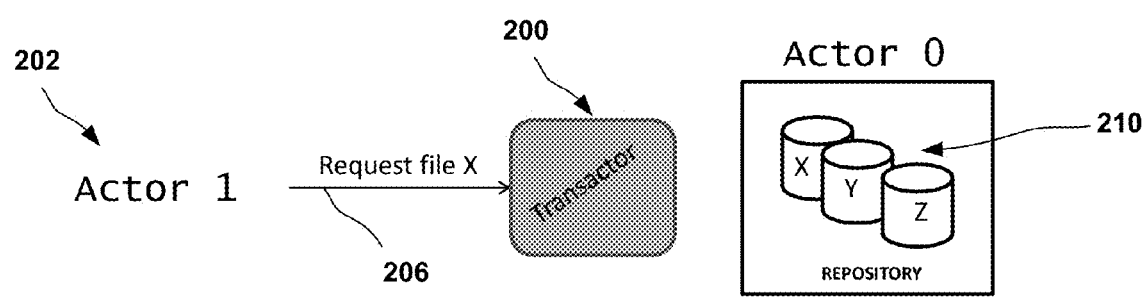
FIGS. 2-7 illustrate exemplary operation of one embodiment of a Transactor included within the GeneTorrent™ system.

Attention is now directed to FIGS. 2-7, which illustrate exemplary operation of one embodiment of a Transactor 200 within a GeneTorrent™ system. As shown in FIG. 2, a first Actor 202 ("Actor 1") makes a first request 206 to the GeneTorrent™ network for file X, such request being received by the Transactor 200. In the present example it is assumed that the only copy of file X is stored at a repository 210.

Figure 3:
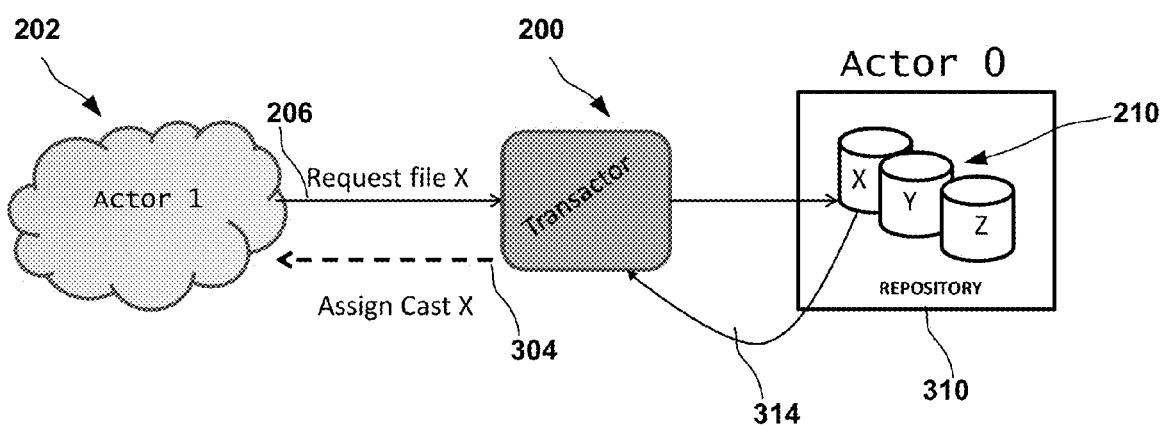

Referring to FIG. 3, the Transactor 200 then locates the actor(s) hosting file X on the network after authorization of Actor 1. Since the Transactor 200 has entitlement rights, Actor 1 is assigned 304 to the Cast X cluster. At this moment Actor 1 is the only actor in the Cast of X. Another Actor 310 ("Actor 0") prepares a GTO file and starts sending 314 random pieces of the file X to Actor 1.

Figure 4:
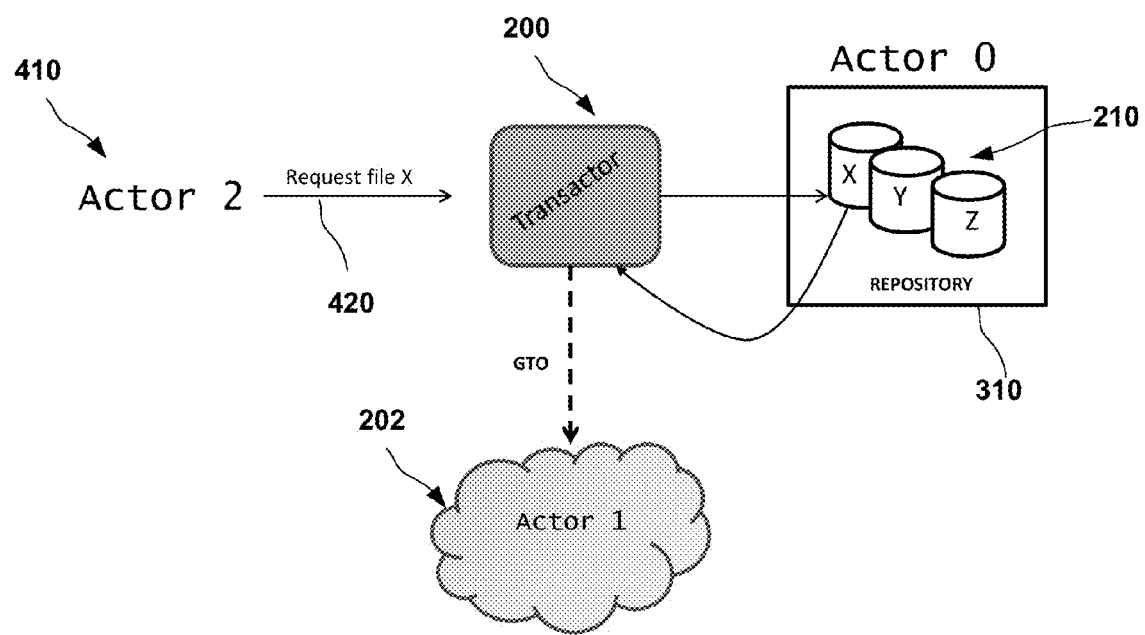

Turning now to FIG. 4, in the next moment an additional actor 410 ("Actor 2") makes a request 420 for file X. Because the Transactor 200 has access rights and is able to assign actors to a particular cast based on the file request, Actor 2 is immediately assigned to Cast X. By this assignment, the Transactor instructs Actor 2 to join Cast X and exchange messages with other actors in the cast in order to determine which parts of file X are possessed by the cast. At this point a GeneTorrent™ instance is initiated with those pieces of file X from Actor 1. Other pieces of the file X are received from either Actor 0 or Actor 1, which remain in communication with each other until the transmission request is complete.

Figure 5:
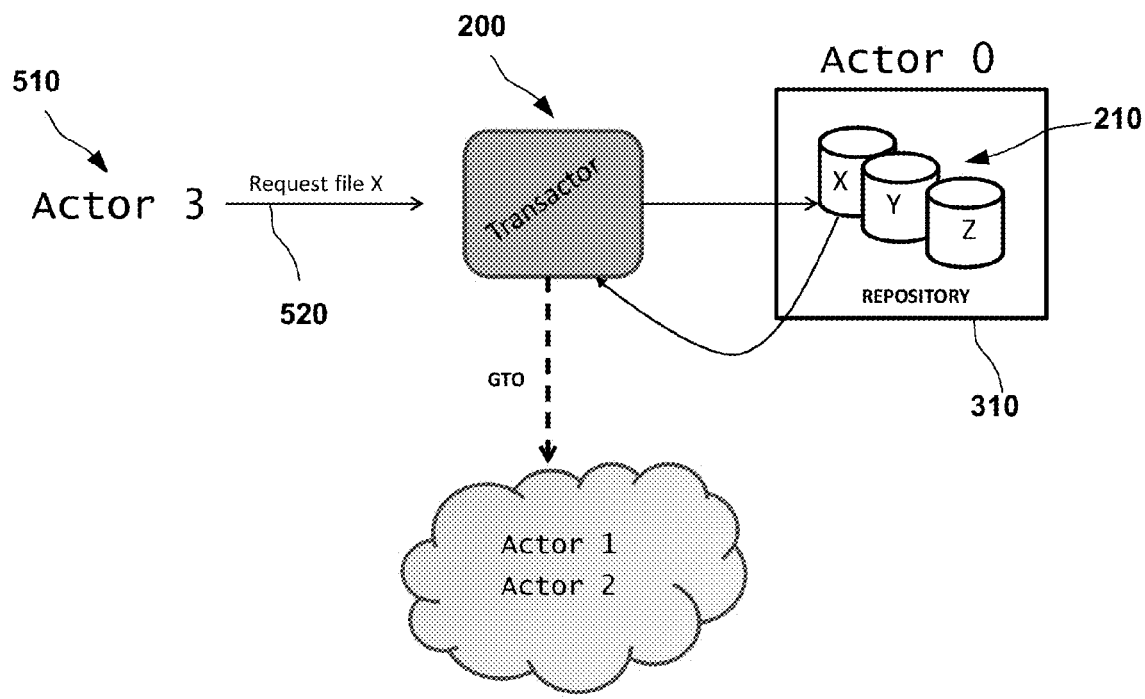

Referring to FIG. 5, a third actor 510 ("Actor 3") makes a request 520 for file X and is assigned by the Transactor 200 to the appropriate cast. At this point Actor 3 begins downloading those instances of file X that exist among the pool of actors in Cast X. The Transactor 200 is thus able to direct each actor to a related cast of actors so as to not overburden the original source of file X. That is, the Transactor 300 directs leechers to a feeder affinity group in order to obtain those portions of a file of interest available from the group without chokepoints.

Figure 6:
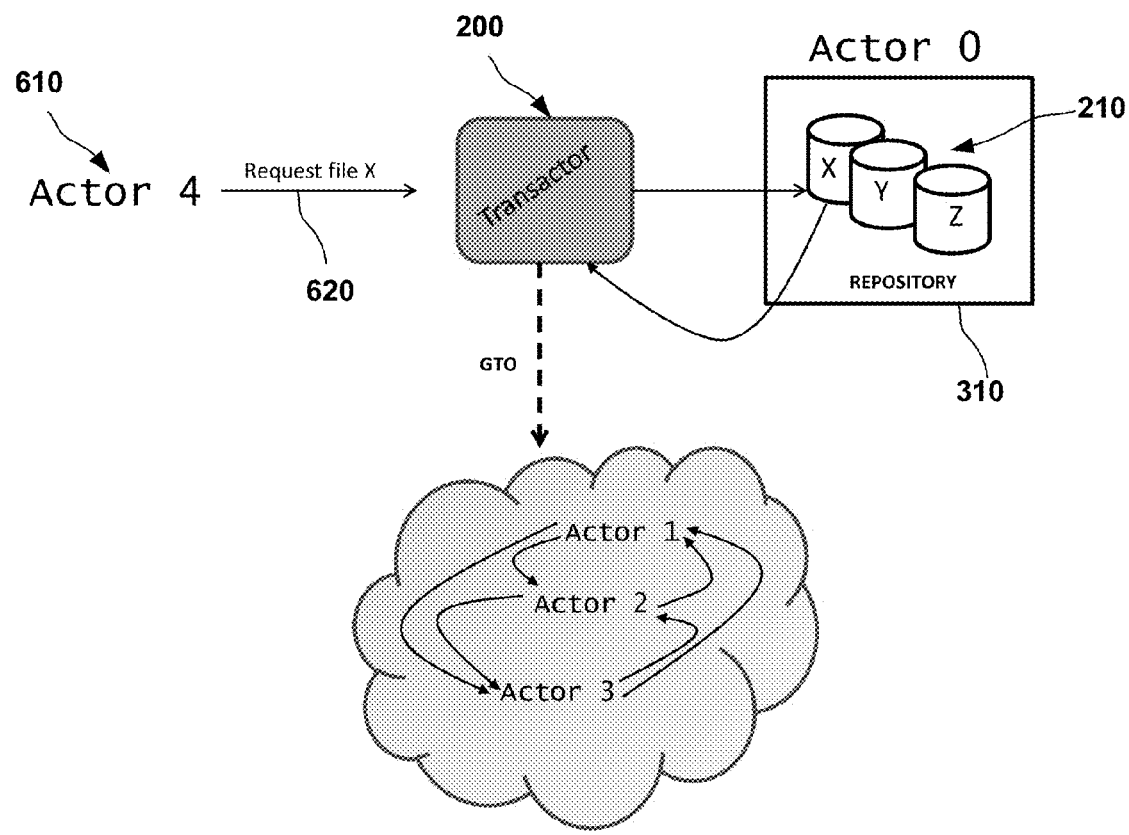

As represented by FIG. 6, a fourth actor 610 ("Actor 4") also makes a request 620 for file X. As is illustrated by FIG. 6, all actors in the cast, i.e., Actor 1, Actor 2 and Actor 3, may function as uploaders as well as downloaders at the same time since random pieces of the file X are being served among all cast members. Since in one embodiment authentication keys are distributed with the parallelized file transfer, all cast members can be confident that all instances of file X that are served among members are from the original source repository.

Figure 7:
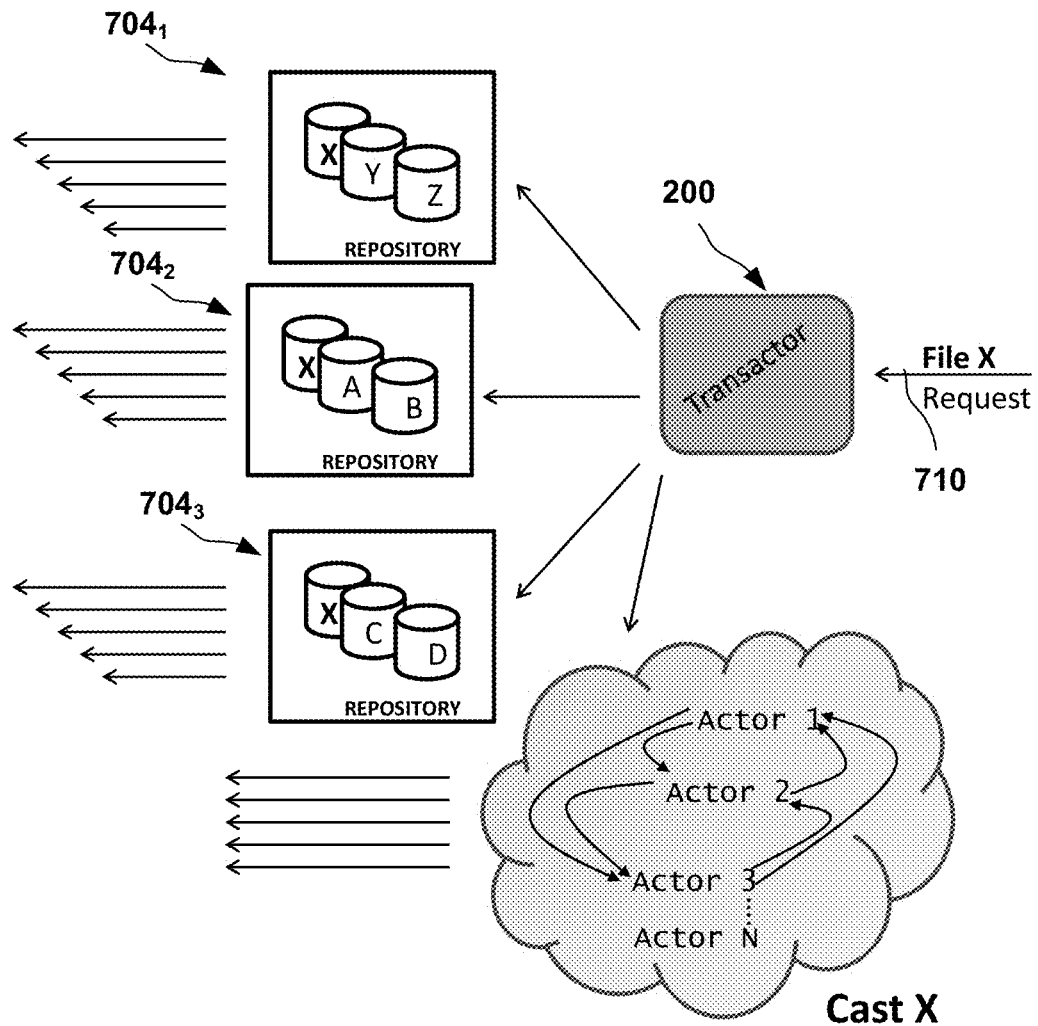

Turning to FIG. 7, it should be appreciated that file X could consist of a file stored in repositories 704 at multiple locations at the time a request 710 is made to download this file on the network. The GeneTorrent™ system can achieve multiple instances of the same file because of the key distribution used to certify copies of file X that it is from one original file. In exemplary embodiments a GeneTorrent™ system can be configured to generate multiple instances of secure parallelized streams from a certified copy of file X from one or more actors to one or more other actors.

In certain embodiments the line of authentication maintained by the Transactor 200 can be to an original copy. In this embodiment the Transactor 200 adds the data certification on top of a "SmartTracker" component that tracks not only who have which file but also tracks biological and clinical knowledge about the files.

For example, using existing protocols it may not be possible to track a specific BAM file and which actors have it or are in the process of obtaining it. However, the SmartTracker may track file specific information contained in these sequence data files on variants, gene expression, copy number variations as well as any disease that might be associated.

In addition, clinical and phenotypic information may be tracked and can be associated with the genome and transcriptome data. In one embodiment the Transactor uses the SmartTracker, conditional access control and a robust encrypt key distribution to assign high affinity actors to a cast based on file X request and essentially on any field of information contained in the sequence data file.

For example, in addition to the Transactor assigning actors to a cast because they are all interested in a particular file X, the actors might be clustered based on information about the file. For example, if the file X is the genome sequence for an individual with disease Y and if it is known that mutations in certain genes on chromosome 17 are associated with the disease, then the Transactor may be more effective in building out a well-defined affinity cast in the early stages of an impending transmission request load to limit any bottleneck.

Bi-Directional Authentication

Embodiments of the GeneTorrent™ protocol disclosed herein provide security for biological sequence data in transit by, for example, running a well-established protocol over Secure Socket Layer (SSL) connections between trusted GeneTorrent™ actors involved in the transfer of file pieces over a network. In one embodiment, the SSL connections will be bi-directionally authenticated in the manner described below.

Figure 8A:
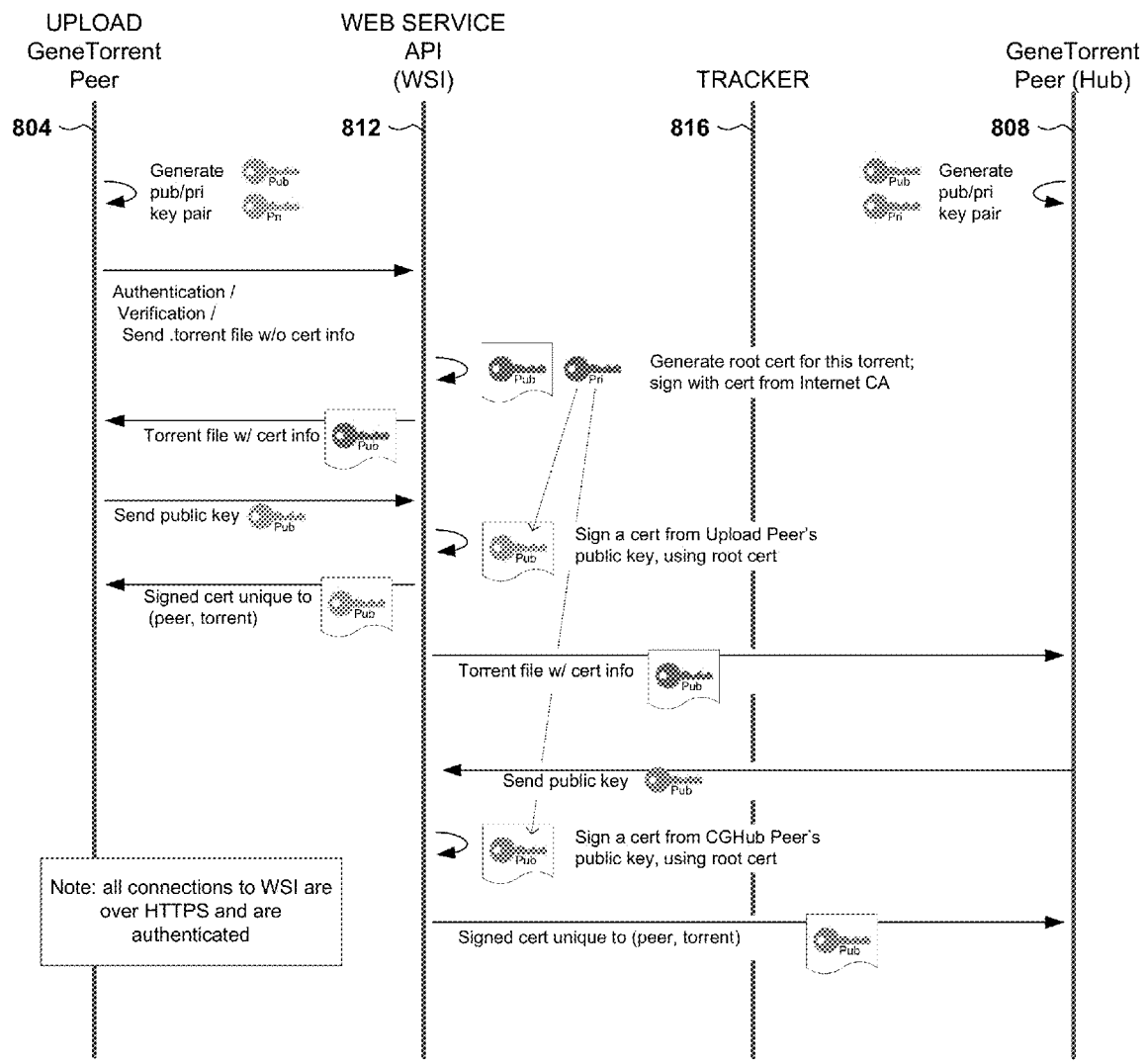
FIGS. 8A-8B illustrate an exemplary sequence of communications occurring between GeneTorrent™ peers executing on a source system(s) and a Genome Data Repository in connection with a file upload operation.
Figure 8B:
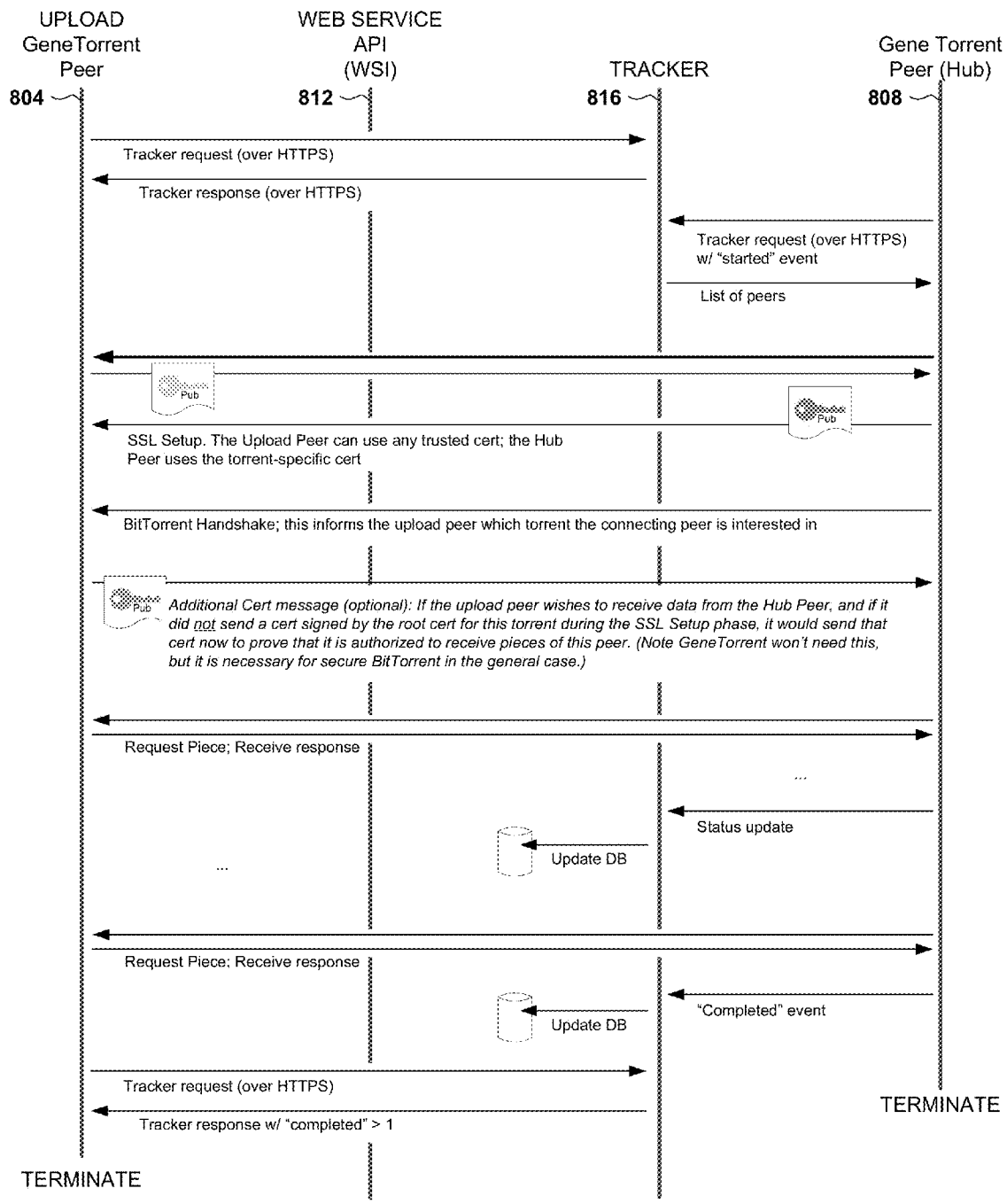

Referring to FIGS. 8A-8B, in a file upload case the GeneTorrent™ client software runs on both a source system(s) 804 and a Hub 808 (e.g., a GDR). In one embodiment the web service interface (WSI) 812 and Tracker 816 run only on the repository systems and mediate the file transfers. As is illustrated by FIG. 8A, in a first stage an exchange of digitally signed certificates takes place.

Certificate Generation

At this point, the uploading source and the GDR have mutually authenticated by exchanging digitally signed certificates that can be traced to a trusted $3^{rd}$ party, i.e., an Internet CA. The certificates are specific to this Gene Torrent Object file and the file it represents, is immune to a replay attack, and is not subject to man-in-the-middle interception.

SSL Session Negotiation

In order to provide enhanced security for the sensitive data on this network, the SSL connections will use the AES-128 cipher, which is a more robust (and FIPS-compliant) cipher than the RC4 cipher typically used.

Parallel Piece Transfers

The typical protocol file transfer takes place, with multiple actors on the side of a repository (e.g., a Genome Data Repository) requesting pieces from an uploader at a source system (e.g., a Genome Sequence Centers (GSC)), until all pieces have been successfully received on the shared file system of the repository.

Session Termination

In one embodiment the SSL session(s) are torn down and the one-time-use Gene Torrent Object file is allowed to expire. The encryption keys that are used to access the data are no longer functional for additional access sessions to this data.

GeneTorrent™ SSL Implementation for File Download

Figure 9A:
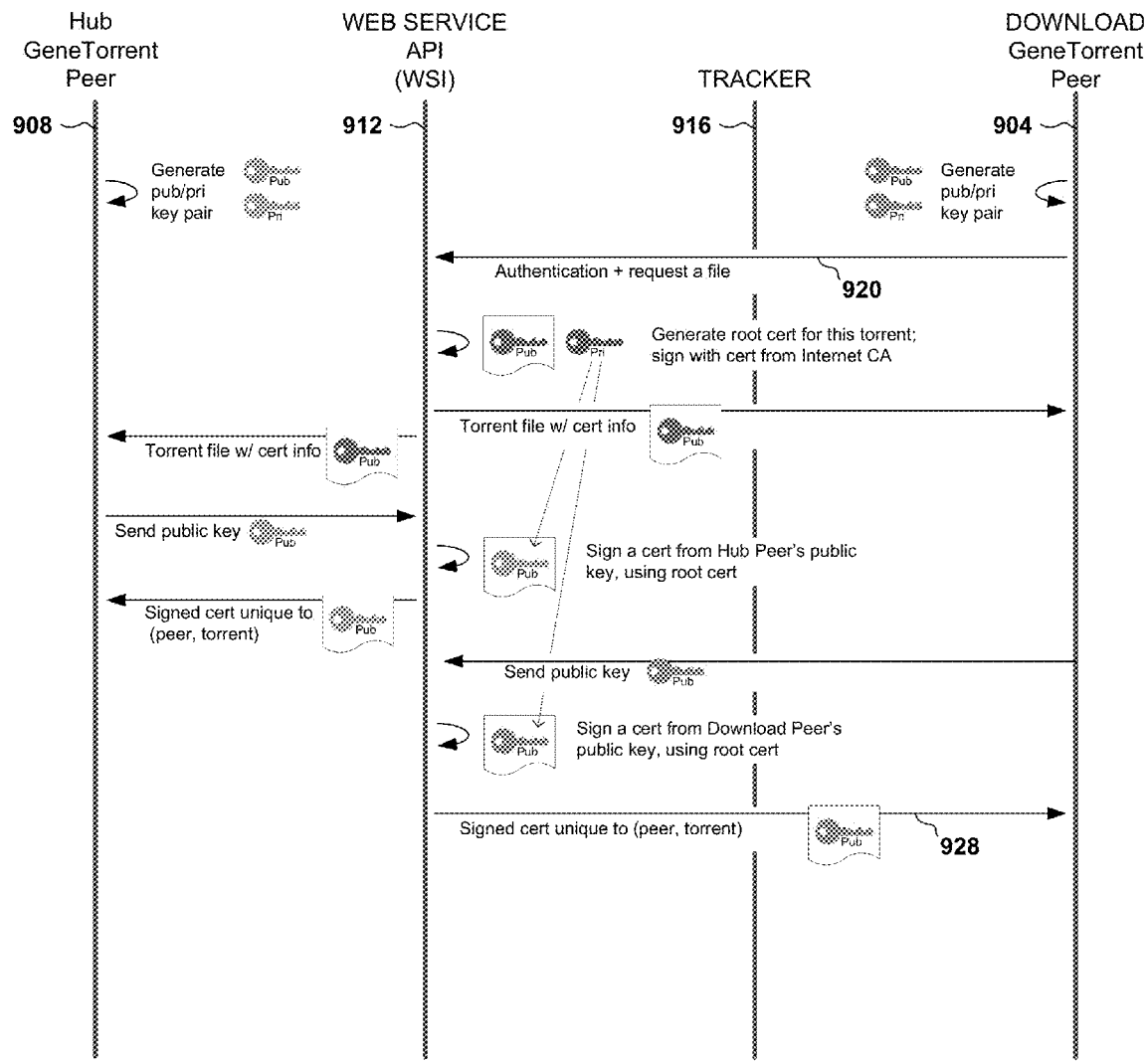
FIGS. 9A-9B provide an illustration of a secure GeneTorrent™ download workflow between client-side GeneTorrent™ data consumers and server-side GeneTorrent™ components.
Figure 9B:
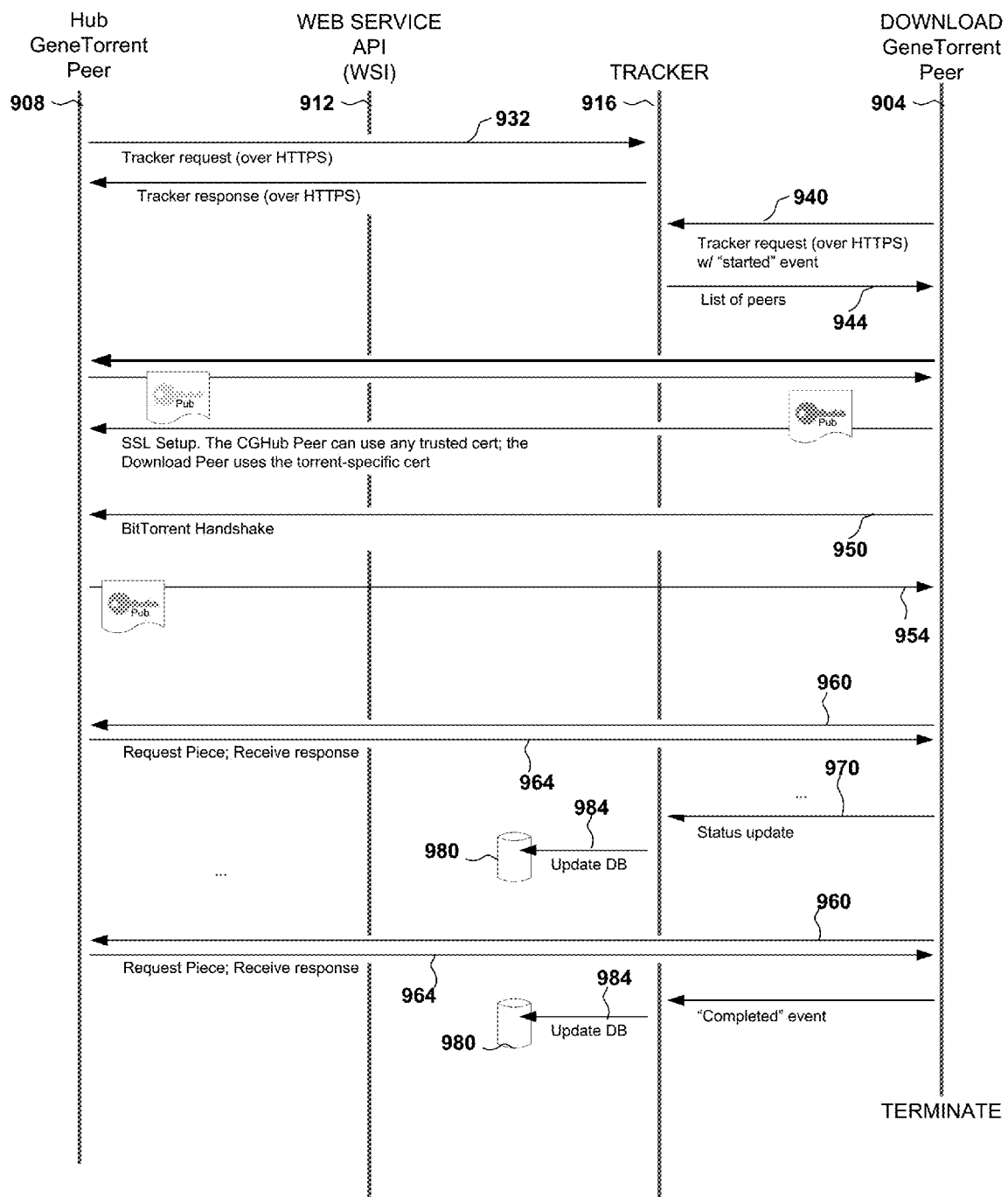

FIGS. 9A-9B provide an illustration of a workflow for a secure GeneTorrent™ file download process between client-side GeneTorrent™ download peers 904 (i.e., data consumers) and the server-side components. In the embodiment of FIGS. 9A-9B these server-side components include a Web services API (WSI) 912 at a Hub 908 (e.g., a GDR), and a Tracker 916.

As shown in FIG. 9A, the workflow is initiated upon a data consumer 904 sending an authentication message and a request for a file to the WSI 912 (stage 920). This initiates the authentication process depicted in FIG. 9A, which culminates in a signed certificate unique to a particular peer and torrent being sent by the WSI 912 to the GeneTorrent™ peer 904 (stage 928).

As shown in FIG. 9B, the GDR 908 continues the download workflow by sending a Tracker request to the Tracker 916 (stage 932). The GeneTorrent™ download peer 904 also sends a Tracker request with a "started" event to the Tracker 916 (stage 940). In response, the Tracker 916 returns a list of peers to the requesting GeneTorrent™ download peer (stage 944). Following performance of an SSL setup procedure involving the GeneTorrent™ download peer 904 and the GDR 908, the download peer 904 initiates a BitTorrent Handshake in order to inform the upload peer, e.g., at the GDR 908, in which torrent the connecting peer may be interested (stage 950). In cases in which the GDR 908 or other upload peer desires to receive data from the download peer 904 and has not sent a certificate signed by the root certificate for the applicable torrent, it sends such a certificate to prove it is authorized (stage 954).

Once the handshaking process has been completed, the download peer 904 requests pieces of the applicable file (stage 960) and receives responses to these requests from the GDR 908 (stage 964). After each piece is received, the download peer 904 provides a status update to the Tracker 916 (stage 970), which then updates its Tracker database 980 (stage 984).

The network flow data that is available on the system can provide powerful statistical correlation data from comparative sequence data analysis. Consider a case where sequence variants data that is transmitted from various GSCs is monitored for quality assurance. In addition, the Tracker 916 may be configured to track pieces of a .gto file to control duplication and distribution of this data.

It is believed that SSL and the necessary certificate management is a novel and key advantage of GeneTorrent™ over public solutions.

GeneTorrent™ Peer Load Balancer

In one embodiment the GeneTorrent™ protocol will be able to scale to accommodate multiple server-side GeneTorrent™ processes, and download requests will be load balanced across processes to optimize server performance. In this embodiment a Load Balancer module will communicate with the WSI 912 over a specified network interface to receive GTO files for each download session. The Load Balancer module will then place the files in the appropriate GeneTorrent™ Peer work queues based on system load and quality of service.

Upon reaching a set threshold level of occurrence of a certain allele this information can be published back to the data consumers as well as all the producers to improve their methods.

Monitoring and Statistics Reporting

Each GDR may maintain a database with full access logs (e.g., which files are uploaded, downloaded and modified by whom) and usage statistics (e.g., average transfer volume and rates, error rates, etc.). In one embodiment these logs will be managed by a Data Manager process using status information obtained from the Tracker database 980. In one embodiment users are permitted to access the data using standard database query and reporting tools.

System Architecture and Principal Components

Figure 10:
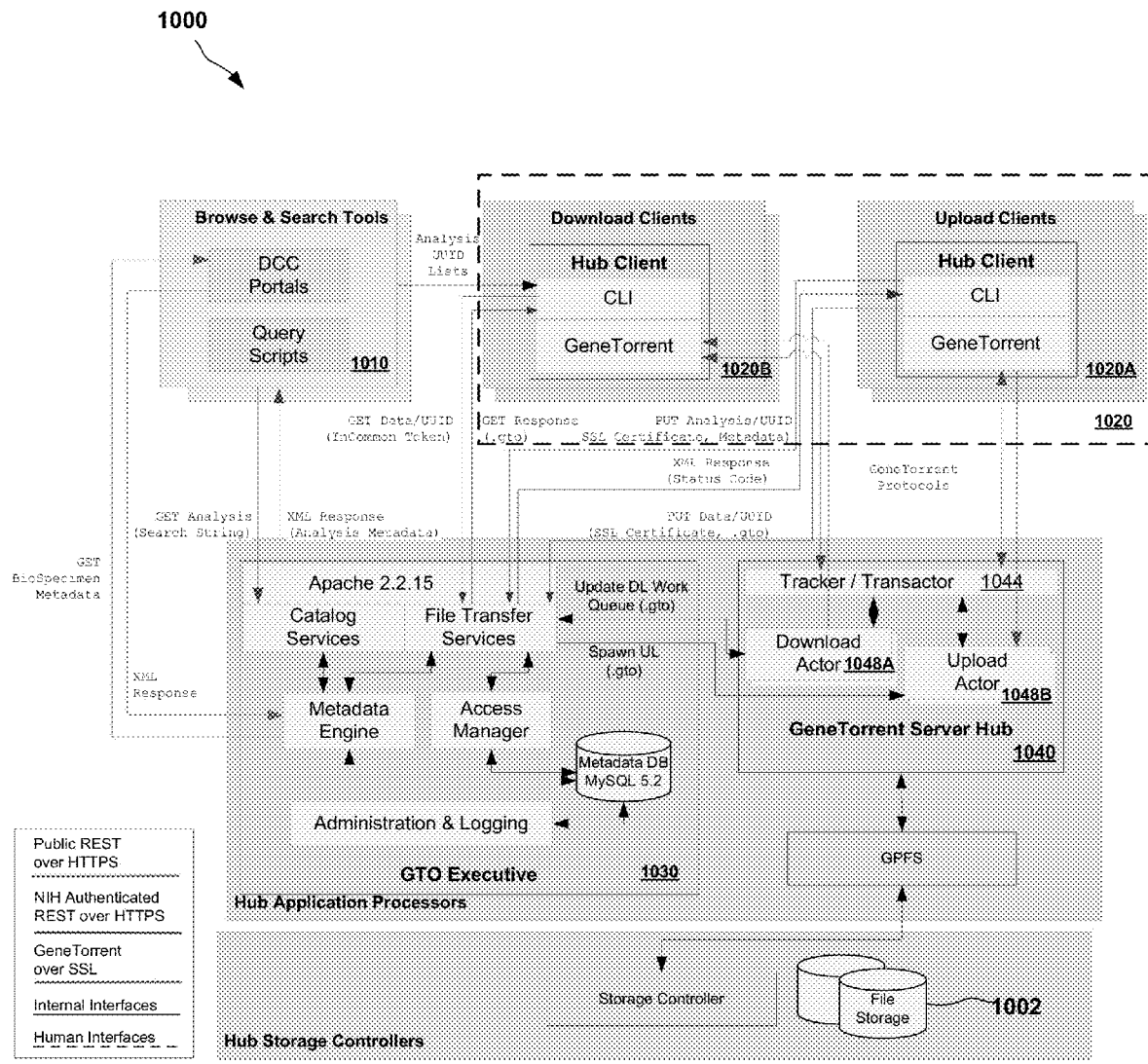
FIG. 10 illustrates an exemplary architecture of a system capable of providing GeneTorrent™ file transfer capability.

Attention is now directed to FIG. 10, which illustrates an exemplary architecture of a system 1000 capable of providing GeneTorrent™ file transfer capability. The system 1000 may operate to transfer files to and from, for example, genome data repositories (GDRs) maintained within storage 1002 or otherwise stored at network locations accessible to the system 1000.

In one embodiment the system 1000 includes the discrete subsystems discussed below, each of which may interface with the others through well-defined, network APIs. In particular, the system 1000 may include a search & browse tools subsystem 1010, a GeneTorrent™ client subsystem 1020, a repository data executive subsystem 1030 and a GeneTorrent™ Server Hub subsystem 1040. It should be appreciated that each subsystem can run on the same or different physical servers or other machines.

The search & browse tools subsystem 1010 may include one or more tools (e.g., DCC Data Portal), Web Browser and/or query scripts for enabling users to search file metadata and find objects for download. The GeneTorrent™ client subsystem 1020 provides, among other things, a command line interface (CLI) for secure, high-performance upload and download. File download functionality is provided by GeneTorrent™ download clients 1020A and file upload functionality is provided by GeneTorrent™ upload clients 1020B. The upload and download clients 1020A and 1020B may run on, for example, POSIX workstations with sufficient storage and performance to be installed at sites (GSCs/GDACs) engaged in the generation and processing of genomic information.

The repository data executive subsystem 1030 includes a server Data Manager configured to run on an application processor. The Data Manager is responsible for ensuring the integrity and security of the data and for providing external interfaces for searching, uploading and downloading data. The Data Manager will generally include a SQL database containing metadata corresponding to the sequence data included within files transferred by the system 1000, user information and system monitoring data.

In an exemplary embodiment external interfaces are implemented as RESTful Web Service Interfaces (WSI). In one embodiment the WSI uses Apache and a Solr search index.

In one embodiment the GeneTorrent™ Server Hub subsystem 1040 includes a Tracker/Transactor process 1044 and multiple GeneTorrent™ peer processes 1048 comprised of one or more download actors 1048A and one or more upload actors 1040B. The Tracker/Transactor process 1044 orchestrates the connections and tracks status for transfers between GeneTorrent™ Actors. This process 1044 also clusters individual actors as participants belonging to a cast of actors in a particular affinity group that are all requesting file X. In one embodiment the Tracker/Transactor process 1044 also determines an actor's cast by the file request, the location of the file (with which actor(s)) and the particular actor's credentials to access the file. The Tracker/Transactor process 1044 may also determine the authentication and entitlement of each actor based on authorization rules and using a secure key distribution scheme.

The repository data executive subsystem 1030 and the GeneTorrent™ Server Hub subsystem 1040 may be collectively referred to herein as the "GT Executive" or the "GT Exec".

In one embodiment users will use a web browser or scripts to query the Web Services interface of the GTO Executive and find the desired objects for download. Users can request downloads for either all the objects within an analysis container or individual files. Because creation of the torrent files requires a non-trivial amount of time to calculate the pieces and checksums, in one embodiment the torrents will be stored in each GDR along with the corresponding data files. This will generally require a separate torrent for each data file.

System Operating Modes

In one embodiment the GeneTorrent™ system 1000 functions in three (3) modes: upload, download, and seeder.

Upload mode is used to upload Gene Torrent Object files to the one or more genome data repositories (GDRs) maintained within storage 1002 or otherwise stored at network locations accessible to the system 1000. Download mode is used to download files from the various GDRs on the network. Seeder mode is a mode used within each GDR to create GeneTorrent™ server instances that seed data to download actors in communication with the system 1000 over one or more networks.

General options (available to all modes):

| | |
|---|---|
| -b<br>--bindIP | Bind IP address (default: All IPs on server) |
| -n<br>--noclean | No clean up. Prevents the application from cleaning up after the transaction completes. |
| -v | Verbose stdout progress reporting (default: |

-continued

| | |
|---|---|
| --verbose | no output for successful processing) |
| -vv | More Verbose stdout progress reporting |
| --moreVerbose | (this is 2 v's, not a W) |
| Upload options: | |
| -a <file name> | Analysis.xml file name, may |
| --analysisFile | include a path |
| -p <path> | Full path to the data files in the analysis |
| --path | file (default: current directory) |
| -s <int value> | Piece size to use when building the gto file |
| --size | (default: 1048576). If not specified, value auto adjusts based on the size of the data file. |
| -t <url> | Tracker URL (this will be made a |
| --trackerURL | default once the CGHub Tracker URL is identified) |
| Seeder options: | |
| -c | Indicates CGHub seeder mode |
| --seeder | |
| -q <path> | Queue directory (file system |
| --queuePath | path) to monitor for new .gto files to seed |
| Download options: | |
| -d <VARIABLE> | Indicates download mode, where |
| --download | VARIABLE is a .gto file, a URI, or an XML file containing a list of URIs. Note that this option may appear multiple times on the command line. |
| -p <path> | Path to save data files in the gto file(s) |
| --path | (default: Current directory). UUID is part of the gto and will always be added to <path>, so data files will be found at <path>/<UUID>. |
| -z <credential file> | Full or relative file name of a file |
| --password | containing the security token for this download (default: ~/.gtUserPass) |

Alternate Operational Control Modes

Although in one embodiment the GeneTorrent™ system may be controlled via a command-line in the manner discussed above, in other embodiments the GeneTorrent™ system may be indirectly controlled by a third party application and/or service. This form of interaction may be characterized as a form of "remote control" in that an entity external to the GeneTorrent™ system directs control of upload and download transfers. The external entity may reside on the same machine(s) as the GeneTorrent™ system components or it may reside in an entirely different network, operating in a command and control fashion from afar.

Additionally, in yet others embodiments of the GeneTorrent™ system may utilize automated batching techniques. In particular, in such embodiments the GeneTorrent™ system may be provided with a list of transfers to perform. This list of commands could be issued either all at once or sequentially by another sub-system and/or component without user interaction.

File Security—Layers of Encryption

The GeneTorrent™ system will generally be capable of ingesting files of any format containing genome and transcriptome sequence data and any additional metadata files that are associated. These files are validated, encoded and encrypted in order to maximize transmission rate.

In one aspect the GeneTorrent™ method may be applied to transfer very large files of biological sequence data along with files containing other data and information having a very specific relationship. It is this information in these files that are encrypted and configured in layers associated with a layered data model.

For example, all of the data that is associated with a whole genome or whole exome sequence data could be encrypted within the same layer with one or more keys. This information may include, without limitation, annotation data concerning functional regions of the genome, genes, promoters, repeat sequences, DNA methylations, SNPs, CNVs, structural variants including chromosomal rearrangements.

A second layer of data would include gene expression data including data from splicing, RNA processing, mRNA-Seq and miRNA-Seq data. Another layer of encrypted data associated with the sequence files may include protein function assay results or protein level measurements. Other layers of encryption may include clinical test results and information on drug metabolism and response.

Yet still other layers of encrypted data might include metadata from various procedures from the extraction of the tissue or cell sample to the analyte preparation methods to the conditions of sequencing to the algorithms used for analysis of the sequence and any molecular pathways, drugs and specific disease associations.

For example, the information that is present in the various layers might be made accessible to based on the consent of the owner and also based on the relevance of the information to the user that is making the request.

Consider the case where the user of the data is a genome data analysis center (GDAC) making a request to use the whole genome sequence data to do an in silico screen for colorectal cancer. The owner of the data or an agent will receive a prompt for consent to use the data and user may then be authorized to access those regions of the genome with association to the specific disease based on layered encryption.

The system is designed to track and coordinate all the data contained within these ancillary files. As a result, each of the various genome data repositories and user/analysis systems in communication over a network may have awareness of the location of data as well as the compute clusters and algorithms that are available. In essence, the encrypted layered data is a component part of how this genomic data network comprised of both genome data repositories and user/analysis systems provides content awareness.

As indicated in Table I, in one embodiment the genome data network is configured in such a manner that authorized users are able to access the various layers of encryption with a consent-based conditional access system.

TABLE I

| Layers | Data Type | Access Level |
|---|---|---|
| Layer 0 | Sequence Files | General |
| Layer 1 | variants | Restricted |
| Layer 2 | Gene Expression | Restricted |
| Layer 3 | Pathways/Drugs | Highly restricted |
| Layer 4 | Disease/disorder | Extreme |
| Layer 5 | Personal data | |

In this embodiment access rights to the data are stored at the repository and controlled by the rules or operating system applicable to the genome data network (which may be referred to herein as the "network operating system"). The determination with regard to access rights is made by the owner or custodian of the data by giving a one-time static consent or doing it dynamically with a different key per request. This will enable distributed, consent-based access to personal health data in a manner consistent with applicable regulations and laws (e.g., HIPAA).

In one embodiment all of the information associated with every file stored within the genome data network is searchable on a network-wide basis. As a consequence, a user with the proper authorization would be able to submit a query relating to any type of information from Table 1 and receive a response identifying all the genome sequence data files on the network that are accessible to the user based on the consent given by the respective owners of the data within the queried files. For example, a query can be made with reference to all of the genome and transcriptome data that has been uploaded to the genome data network during a predetermined period (e.g., within the last 60 days).

In this case, the response to the query could come from multiple genome data local area networks (gLANs) included within the genome data network. The network operating system may be configured to monitor the consent for access to data and user authorization and be able to effectively authenticate users.

Figure 11:
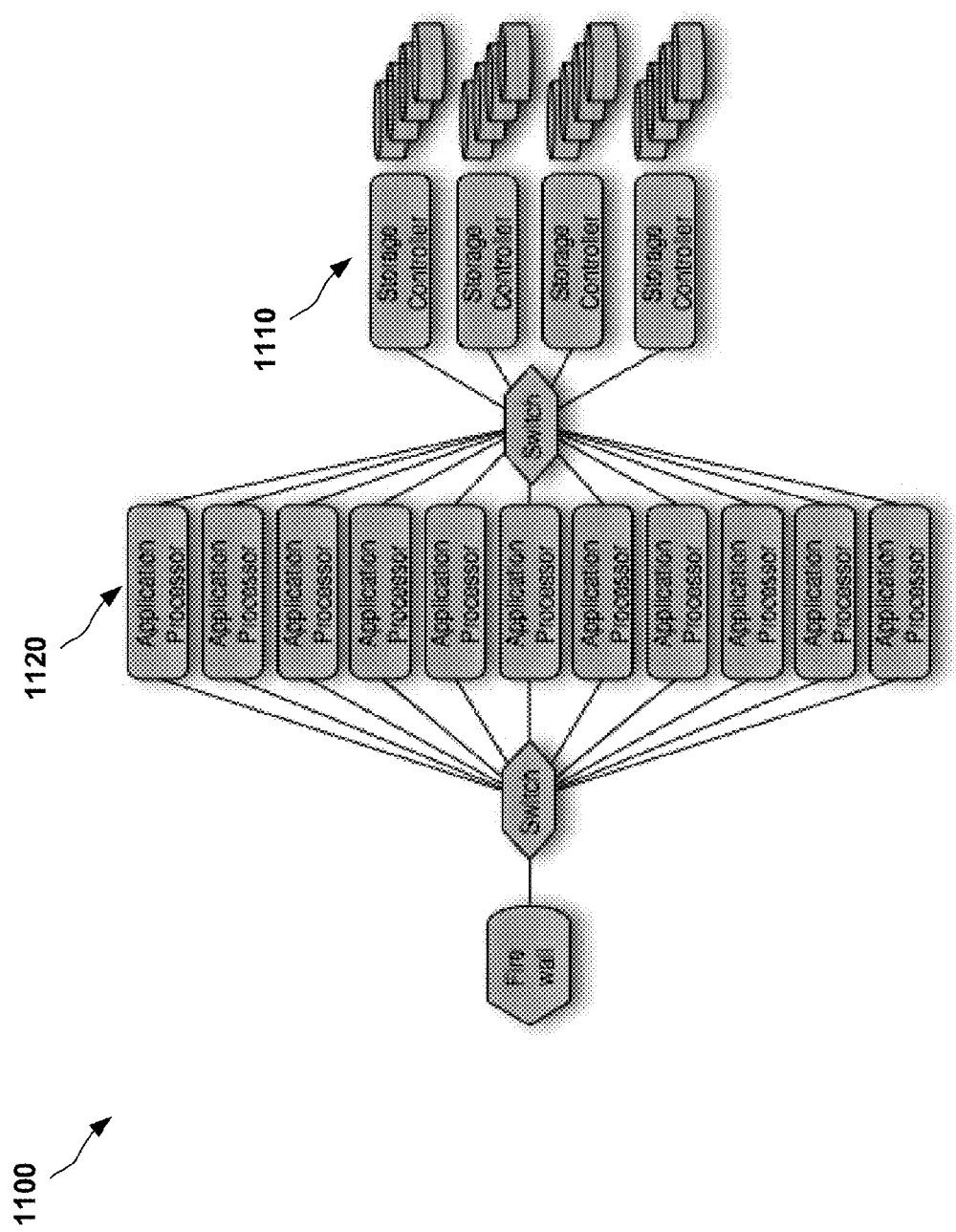
FIG. 11 illustrates a data repository comprising high-speed fiber optic storage and computing infrastructure capable of facilitating the acquisition, secure storage, searching, and secure sharing of genome sequence data and phenotype metadata.

Attention is now directed to FIG. 11, which provides a block diagrammatic representation of an exemplary genome data repository 1100 capable of being used to store genomic and other data accessible to users of a genome data network. The repository 1100 may include high-speed fiber optic storage and computing infrastructure capable of facilitating the acquisition, secure storage, searching, and secure sharing of genome sequence data and phenotype metadata with authorized to access. In one embodiment the repository 1100 provides secure transfer and storage of genome and phenotype information by authorized users and supports multiple simultaneous high capacity transfers across multiple 10 gigabit/second links.

As shown, the repository 1100 includes a plurality of storage controllers 1110 that may be configured to storage relatively large amounts of genomic data. For example, the storage controllers 1110 may be designed to initially store at least 500 Terabytes of genome data (scalable to 5 Petabytes of genome data and architected for 20 Petabytes of genome data). The repository also includes a cluster of application processors 1120 that provide high performance file transfer, security access control, fault protection and workflow monitoring.

Transfer and Ingestion Software

Sequence Producing Centers are anticipated to be a primary source of sequence data. At such Centers, digital representations of biological samples are generated by processing such samples. Optionally, research centers may also upload genome data. In addition, phenotype information and high-level features derived from the raw sequence, the metadata, is produced at the DCC and other sources. In one embodiment software and associated hardware will be located at these centers to perform a genome sequence transfer and ingestion processes. Such software will generally be capable of checking data format and validity prior to initiating uploading to a genome data repository. The software will also preferably perform transfer of genome and metadata information to the data repository and support high capacity transfers at very high data rates (e.g., 10 Gigabits/second).

Genome and Phenotype File Type, Sizes, and Organization

In one embodiment data may be organized and grouped within the data repositories included within a genome data network as follows:
cancer type (lung, ovarian, etc), about 25 types
batch (tumor/normal pairs are done in batches of about 100 cases, 5 batches per cancer type)
case/sample ID within the batch (e.g. ID=TCGA-06-145)
The case/sample ID will have various extensions for the various types of files made for each case:
tumor whole genome sequence file (250 GB),
tumor exome sequencing file (25 GB),
tumor RNA-seq file (<120 GB),
tumor miRNA-Seq files
tumor CNV files
tumor methylation file (<1 GB),
blood normal whole genome file (250 Gb),
blood normal exome file (25 Gb),
blood normal RNA-seq file (<120 GB),
blood normal miRNA-Seq files
blood normal CNV files
blood normal methylation file (<1 GB),
adjacent normal whole genome file (250 GB) and
adjacent normal exome file (25 GB)

Digital Data Repository Configuration

Figure 12:
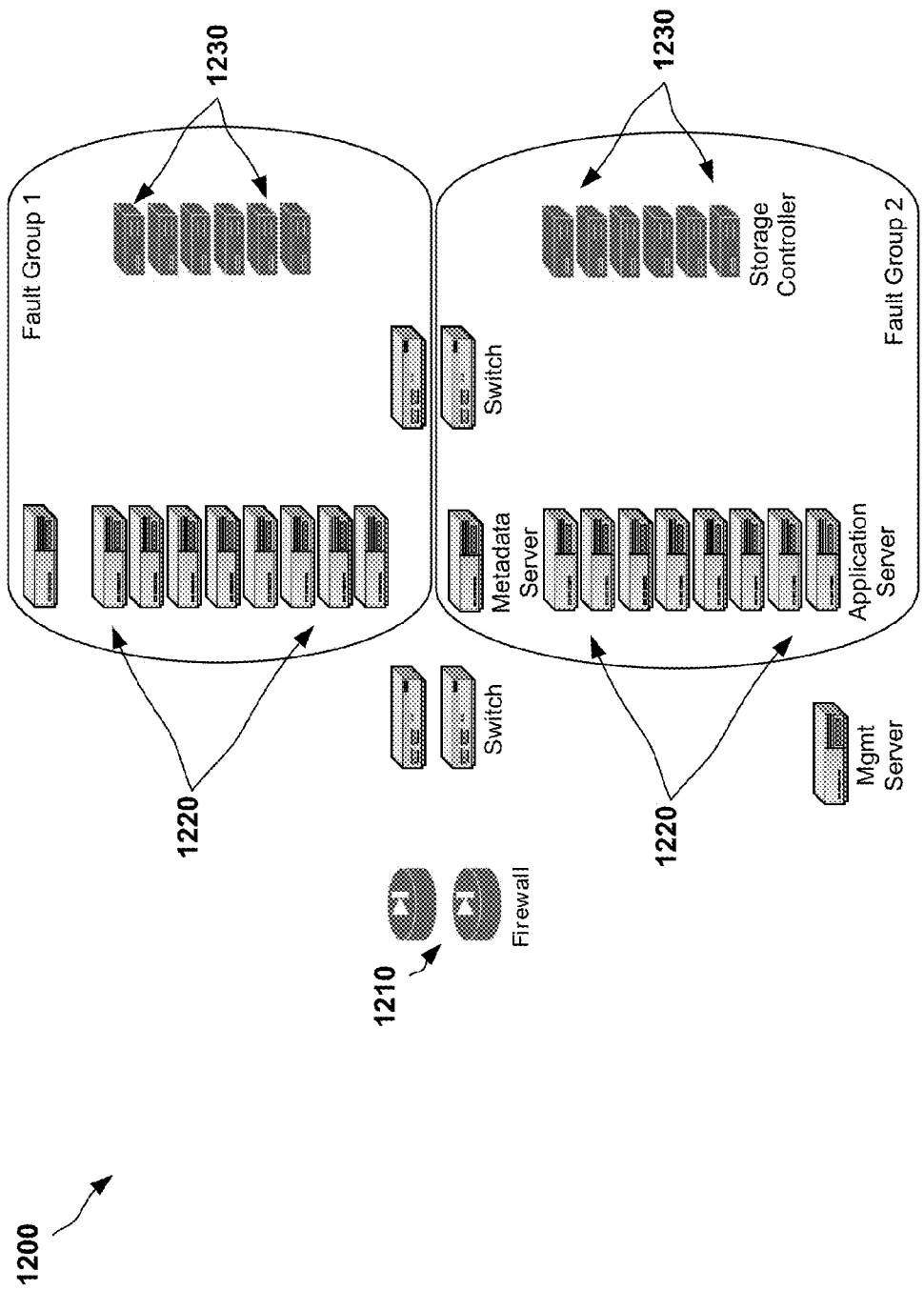
FIG. 12 depicts an implementation of data repository equipment comprised of several levels including a firewall level, application array level, and storage array level.

Referring to FIG. 12, in one embodiment the equipment used to implement an exemplary digital data repository 1200, such as a genome data repository, may be grouped within three main levels: (1) firewall 1210, (2) application array 1220, and (3) storage array 1230. A 10 Gbps Ethernet Switch may be used to interconnect the equipment. Separate VLANs and layer 3 filters may be used to logically separate the levels of the system to maximize performance and prevent unauthorized access.

In one embodiment the firewalls provide Layer 4 protection for the datacenter from the external network. The application array provides the primary logic for user access to the storage, including access control, catalog perusal, and file transfer. The storage array provides scalable, high performance, reliable access to high capacity disks. All levels may be connected over LOGE networks, separated into two networks partitioned for storage and application. The system is also partitioned into two separate fault groups wherein a storage failure can be isolated.

Figure 13:
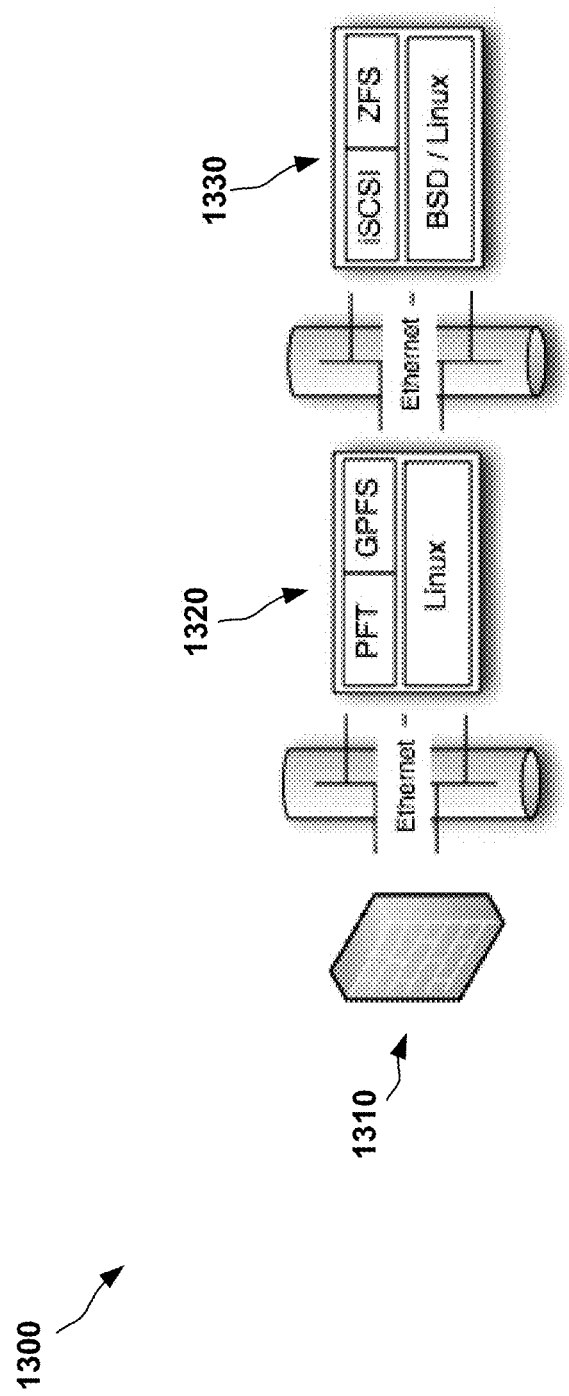
FIG. 13 illustrates an exemplary software configuration associated with the multi-level data repository of FIG. 12.

Referring to FIG. 13, in one embodiment the software configuration of the levels of the exemplary digital data repository 1300 consist of the following:

1) Firewall 1310—dedicated appliance or Linux based firewall such as Vyatta.

2) Application Server 1320—Linux Operating System, GPFS, parallel file transfer (PFT) application, Apache, node.js. Additional servers are dedicated for file system metadata and cluster management.

3) Storage Controller 1330—BSD or Linux, ZFS exporting iSCSI volumes.

In one embodiment software at sequence producing centers (e.g., at genome sequencing centers (GSCs)) will ensure that files are properly formed and content meets acceptable criteria before upload operation can commence. This ensures that data reaching the applicable digital data repository will be usable and reduces the troubleshooting time in identifying and correcting incorrect data.

Cloud-Related Applications

A number of organizations have developed "cloud-based" services to enable enterprise and other organizations to manage data and applications within a network-based, i.e., "cloud" environment. For example, Microsoft's Windows Azure offers multiple services to assist customers in managing their data in the cloud. In particular, the SQL Database service offering enables entities to quickly develop and manage applications in the cloud.

However, one impediment to utilization of such cloud-based services by, for example, enterprise organizations is the difficulty in transferring large data files between an enterprise's data center and the cloud. As mentioned above, the additive increase/multiplicative decrease algorithm used by TCP to avoid congestion and control bandwidth usage can impede the transmission rate of very large sequence data files, even on high-speed networks. For at least this reason conventional protocols for transferring bulk data (e.g., data files) tend to experience potentially severe performance degradation over available Internet connections. When TCP-based or other conventional techniques are used, such transfer to and from the cloud is often characterized by slow speed, high failure rates, and high risk of data corruption. Transfer of large amounts of data often occurs when, for example, an enterprise initiates a very large initial upload of data from a data center to a cloud service provider, a periodic back up is commenced, or when multiple sources of data are consolidated and made available through the cloud.

Figure 14:
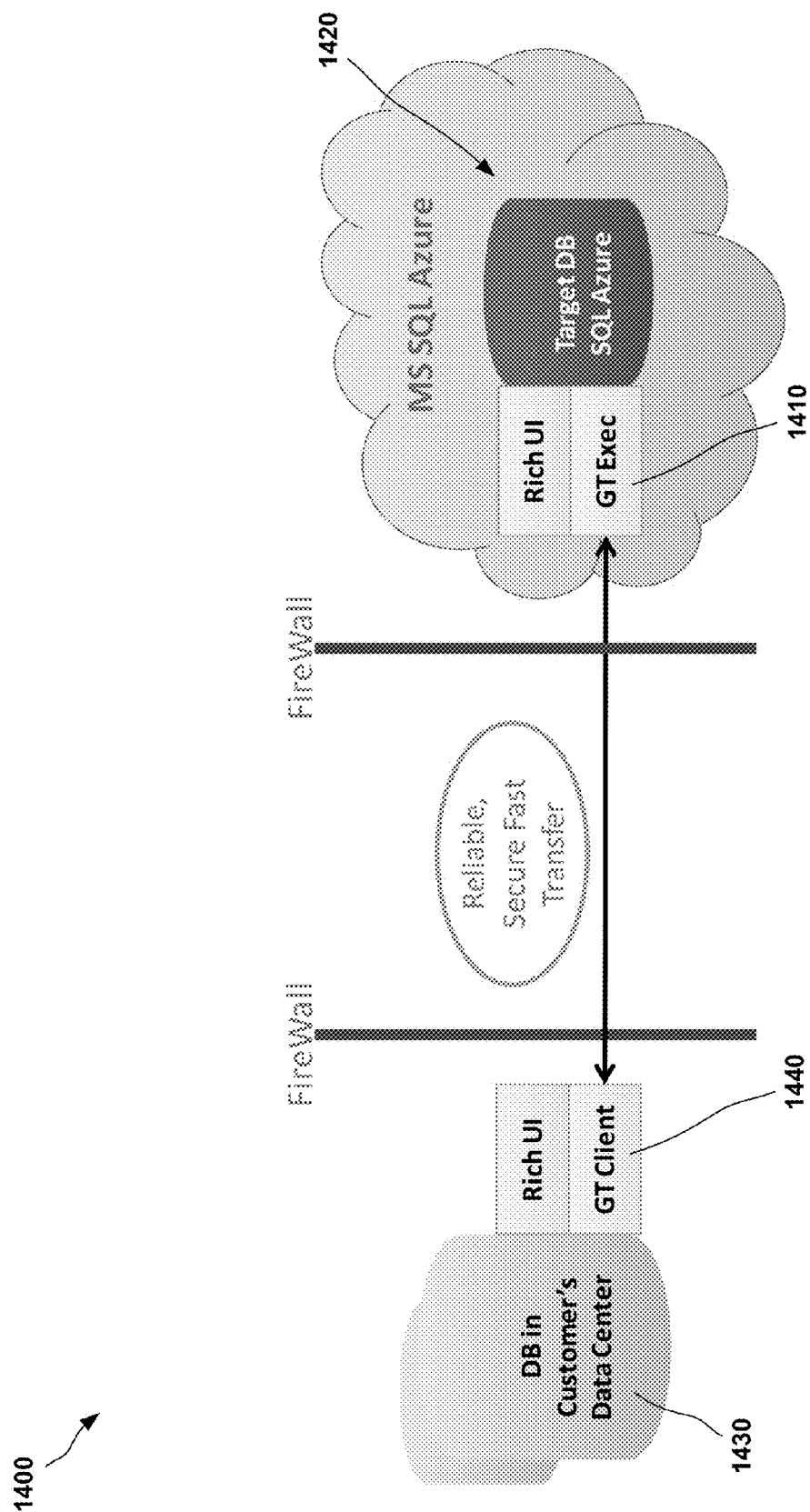
FIG. 14 illustrates an implementation of an GeneTorrent™ file transfer system within a cloud-based environment.

Attention is now directed to FIG. 14, which illustrates an implementation of the GeneTorrent™ system 1400 within a cloud-based environment. As shown, a GT Executive 1410 ("GT Exec") runs within an instantiation of a cloud-based database 1420 (e.g., a Windows Azure database) and functions as a "file server". In particular, the GT Exec 1410 may handle authentication and authorization and be designed to function as a federated single sign-on system. A metadata catalog within the GT Exec may be customized and managed.

The GeneTorrent™ system enables a cloud-based database or other cloud-based platform to facilitate offering high-speed transfer of large data files as a service. For example, the GT Exec may provide a customized portal for each customer or other user to receive requests for data transfers from a particular data center 1430 to a cloud-based database, or vice-versa. In one embodiment the GT Exec would cooperate with a GT client 1440 within each data center to facilitate transfers of large data files to and from the cloud-based database.

In summary, at least the following are included among the methods and systems for secure, high-speed file transfer of very large files disclosed herein:

A method for transmitting (e.g., at >10 Gbits speed) BAM and xml files from an optical network to storage arrays using a client configured to transmit parallel streams of a file to a switch (e.g., a 10 Gbits switch) capable of sending different portions of the file to multiple file servers running the same file transfer application. A second switch may also be provided for high-speed access to multiple storage clusters.

A method for storing genome sequence files and metadata files that render them searchable by any attribute that is a field in the header or xml file An apparatus for receiving a high-speed transmission of parallelized bit streams and evenly distributing the large file transfer across a series of application servers through a high speed switch.

A method for monitoring the patient consent status and the authorized user of such phenotypic and genomic data.

A method of formatting genomic data with the germline variants data stored in one layer of a data model while somatic mutation data are stored in a different layer of the data model.

A method for storing a particular set of molecular data that is associated with a certain disease separately from other molecular expression data and variants data that is associated with other diseases.

A method for the initiating the high-speed transfer of genomic data by configuring a client program at a genome sequencing center to prompt a data repository to receive a highly-parallelized transfer of genome data.

A method for encryption of genome data in layers to make the data accessible based upon multiple levels of sensitivity.

A method for encrypting genome sequence data wherein at least one layer consists of validated germline mutation call, repeat sequences and genotyping variants data.

A method for encrypting genome sequence data wherein at least one layer of encryption consist of validate somatic mutations found in the genome of tissue/cell of a tumor.

A method for encrypting genome sequence data wherein at least one layer of encryption consist of validate somatic mutations found in the genome of diseased tissue such as brain.

A method for encryption of transcriptome sequence data in layers to make the data accessible based upon multiple levels of sensitivity.

A method for encrypting transcriptome sequence data wherein at least one layer consist of validated germline mutation call, repeat sequences and other genotyping variants data.

A method for encrypting transcriptome sequence data wherein at least one layer of encryption consist of validate somatic mutations found in the genome of tissue/cell of a tumor.

A method for encrypting transcriptome sequence data wherein at least one layer of encryption consist of validate somatic mutations found in the genome of diseased tissue such as brain.

A method to encrypt ancillary data associated any biological sequence data in a configuration consistent any combination of information types.

An entitlement control system that uses data owner consent and user authorization to regulate transactions involving sequence data.

A method of using a highly distributed conditional access system to secure biological sequence and related data files.

A method for using a highly distributed conditional access system to regulate the access to data between at least two transaction points.

A method for encoding biological sequence data files to grant conditional access based on user consent.

A method to control and coordinate secure transactions by distribution of public/private keys for use with GeneTorrent™ technology configured to send parallelized data streams from a source actor to a destination.

A method to transmit multiple secure instances of a single Gene Torrent Object (GTO) file over parallel streams. The method includes using software clients for uploading and downloading the genome data files. The method may include authorizing a user's request to download a particular file based upon, for example, the consent of the file owner to a transfer of the file. The method may further contemplate that encryption keys are exchanged between trusted partners on the network for security.

A process for configuring a single biological data file as multiple instances on more than one server and transmitting the file to one or more network nodes.

A method of entitlement control that allows parallel streams of one universally identifiable GeneTorrent™ file from more than one actors to more than one node on a network based on static and dynamic consent rules.

A computer-implemented process that accepts binary alignment map or a related formatted biological sequence data file and transmits it over a network in multiple parallel instances.

Specific details are given in the above description to provide a thorough understanding of the embodiments. However, it is understood that the embodiments may be practiced without these specific details. For example, circuits or other apparatus may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, virtualization systems or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure. It is intended that the following claims and their equivalents define the scope of the systems and methods described herein.

We claim:

1. A method for facilitating transfer of an electronic file over a network, the method comprising:
   sending a first portion of the electronic file from a first server instance of the plurality of server instances;
   sending a second portion of the electronic file from a second server instance of the plurality of server instances wherein the first portion and the second portion of the electronic file are respectively included within first and second parallel streams;
   receiving information relating to a second portion of the electronic file sent by the second server instances; and
   sending a third portion of the electronic file from the first server instance;
   wherein the third portion is different from the second portion and is included within the first parallel stream.

2. The method of claim 1 further including reading the first portion of the electronic file from a database containing the electronic file.

3. The method of claim 2 further including reading the third portion of the electronic file from the database.

4. The method of claim 1 further including providing, to the second server instance, information relating to the sending of the first portion of the electronic file.

5. The method of claim 1 further including receiving information relating to a fourth portion of the electronic file sent by a third server instance wherein the third portion is different from the fourth portion.

6. The method of claim 5 further including sending, from the first server instance, a fifth portion of the electronic file wherein the fifth portion is different from the second portion and the fourth portion.

7. The method of claim 1 wherein the first portion of the electronic file is sent to a first receiving node different from a second receiving node configured to receive the second portion of the electronic file.

8. The method of claim 1 wherein the third portion of the electronic file is sent to the first receiving node.

9. The method of claim 1 further including:
   receiving information relating to corruption of the first portion of the electronic file; and
   resending the first portion of the electronic file from the first server instance.

10. The method of claim 1 wherein the electronic file includes genomic information.

11. The method of claim 10 wherein the genomic information comprises information associated with a plurality of layers of a data model.

12. The method of claim 11 wherein the first portion, the second portion and the third portion of the electronic data file are each associated with a first of the plurality of layers.

13. The method of claim 11 wherein the first portion of the electronic file is associated with a first of the plurality of layers and the second portion of the electronic file is associated with a second of the plurality of layers.

14. A method for facilitating transfer of an electronic file over a network, the method comprising:

generating first encrypted file information by encrypting a first portion of the electronic file using first encryption information;

generating second encrypted file information by encrypting a second portion of the electronic file using second encryption information different from the first encryption information;

sending, from a first server instance and a second server instance, the first encrypted file information and the second encrypted file information in first and second parallel streams; and sending third encrypted file information from the first server instance wherein the third encrypted file information is generated using a third portion of the electronic file;

wherein the third portion is different from the second portion and wherein the third encrypted file information is included within the first parallel stream.

15. The method of claim 14 wherein the first encryption information includes a first encryption key and the second encryption information includes a second encryption key.

16. The method of claim 14 wherein the electronic file includes genomic information.

17. The method of claim 16 wherein the genomic information comprises information associated with a plurality of layers of a data model.

* * * * *